(12) United States Patent
Nickel et al.

(10) Patent No.: US 6,953,570 B2
(45) Date of Patent: Oct. 11, 2005

(54) PORPHYRINS WITH ENHANCED MULTI-PHOTON ABSORPTION CROSS-SECTIONS FOR PHOTODYNAMIC THERAPY

(75) Inventors: Eric Nickel, Marietta, GA (US); Charles W. Spangler, Livingston, MT (US); Aleksander Rebane, Bozeman, MT (US)

(73) Assignee: Montana State University, Bozeman, MT (US)

( * ) Notice: Subject to any disclaimer, the term of this patent is extended or adjusted under 35 U.S.C. 154(b) by 137 days.

(21) Appl. No.: 10/225,303

(22) Filed: Aug. 22, 2002

(65) Prior Publication Data

US 2003/0105070 A1 Jun. 5, 2003

Related U.S. Application Data

(60) Provisional application No. 60/348,393, filed on Jan. 16, 2002, and provisional application No. 60/313,815, filed on Aug. 22, 2001.

(51) Int. Cl.$^7$ ........................... A61B 10/00; A61B 5/00; A61B 8/00
(52) U.S. Cl. .................... 424/9.61; 424/1.11; 424/1.65; 424/9.1; 424/9.6; 424/9.362
(58) Field of Search ............................. 424/1.11, 1.65, 424/9.1, 9.3, 9.5, 9.6, 9.7, 9.8, 9.4, 9.61, 9.362; 540/145

(56) References Cited

U.S. PATENT DOCUMENTS

| 5,929,105 A | 7/1999 | Sternberg et al. ............ 514/410 |
| 6,123,923 A | 9/2000 | Unger et al. ................ 424/9.52 |
| 6,136,841 A | 10/2000 | Platzek et al. .............. 514/410 |

FOREIGN PATENT DOCUMENTS

| WO | WO 9627798 | * | 9/1996 |
| WO | WO 97/20846 | | 6/1997 |
| WO | WO 98/50034 | | 11/1998 |
| WO | WO 99/59641 | | 11/1999 |

OTHER PUBLICATIONS

Kinoshita et al (Review of Scientific Instruments, 2000, 71 (9), pp. 3317–3322).*
Albota, M., et al., "Design of organic molecules with large two–photon absorption cross–sections", *Science*, 281, 1653–1656 (1998).
Bhawalkar, J. D., Kumar, N. D., Zhao, C.–F. & Prasad, P. N., "Two–photon photodynamic therapy", *J. Clin, Lasers Med. Surg.*, 15, 201–204 (1997).
Bonnet, R., "Photosensitizers of the porphyrin and phtalocyanin series for photodynamic therapy", *Chem. Soc. Rev.*, 24, 19–33 (1995).
Cheong, Wai–Fung, Prahl, S.A., & Welch, A.J., "A review of the optical properties of biological tissues", *IEEE J. of Quantum Electron*, 26, 2166–2185 (1990).

Cumpston, B. H., et al., "Two–photon polymerization initiators for three–dimensional optical data storage and microfabrication", *Nature*, 398, 51–54 (1999).
Drobizhev, M., Karotki, A. & Rebane, A. "Persistent spectral hole burning by simultaneous two–photon absorption", *Chem. Phys. Lett.* 334, 76–82 (2001).
Fisher, W. G., Partridge, W. R., Jr., Dees, C. & Wachter, E. A., "Simultaneous two–photon activation of type–I photodynamic therapy agents", *Photochem. Photobiol*, 66, 141–155 (1997).
Frederiksen, P. K., Jorgensen, Ogilby, P. R., "Two–photon photosensitized production of singlet oxygen", *J. Am. Chem. Soc.*, 123, 1215–1221 (2001).
Goyan, R. L. & Cramb, D. T., "Near–infrared two–photon excitation of protoporphyrin IX: photodynamics and photoproduct generation", *Photochem. Photobiol.*, 72, 821–827 (2000).
Henderson, B. W. & Dougherty, T. J., "How does photodynamic therapy work?", *Photochem. Photobiol.* 55, 147–157 (1992).
Karotki, A., et al., Efficient Singlet Oxygen Generation Upon Two–photon Excitation of New Porphyrin with Enhanced Nonlinear Absorption, IEEE Jour. on Sel. Topics in Quantum Elec., vol. 7, No. 6, Nov. 2001.
Kershaw, S., "Two–photon absorption, In: Characterization Techniques and Tabulations for Organic Nonlinear Optical Materials", M. G. Kuzyk, C. W. Dirk, Eds., Marcel Dekker, New York, 1998.
König, K., "Multiphoton microscopy in life sciences", *J. Microsc.*, 200, Pt. 2, 83–104 (2000).
Spangler, C. W., "Recent developments in the design of organic materials for optical power limiting", J. Mater, Chem. 9, 2013–2020 (1999).
Sundholm, D. "Density functional theory study of the electronic absorption spectrum of Mg–porphyrin and Mg–etioporphyrin–I", *Chem. Phys. Lett.*, 317, 392–399 (2000).

* cited by examiner

*Primary Examiner*—Dameron L. Jones
(74) *Attorney, Agent, or Firm*—Morgan, Lewis & Bockius LLP

(57) ABSTRACT

A method of increasing the multi-photon absorption cross-section of a porphyrin-based photosensitizer by attaching at least one TPA-chromophore at the meso- or beta-positions of a porphyrin structure of the porphyrin-based photosensitizer, and at least one intersystem crossing enhancing substituent to meso- or beta-positions of a porphyrin structure of the porphyrin-based photosensitizer, to thereby increase multi-photon absorption cross-section of the porphyrin-based photosensitizer to at least about 30 GM units at about its maximum wavelength for two-photon absorption. The TPA-chromophore is selected from a group of π-conjugated structures. The resulting porphyrin-based photosensitizer absorbs two photons of radiation in the range of about 700 nm to about 1300 nm.

16 Claims, 21 Drawing Sheets

R$^1$ = -L-TPA, -H, -Ar, -(CH$_2$)nCH$_3$, -CH=CH$_2$, -(CH$_2$O)n-G, -t-Butyl, or -C(O)OG;

R$^2$ = -L-TPA, -H, -Ar, -(CH$_2$)nCH$_3$, -CH=CH$_2$, -(CH$_2$O)n-G, -t-Butyl, or -C(O)OG;

R$^3$ = -L-TPA, -H, -Ar, -(CH$_2$)nCH$_3$, -CH=CH$_2$, -(CH$_2$O)n-G, -t-Butyl, or -C(O)OG;

R$^2$ and R$^3$ may also be linked by a C$_4$H$_4$ group;

M = 2 H atoms or a metal ion;

n is independently an integer ranging from 1 to 20;

G = H, or a C$_1$ to C$_{20}$ alkyl;

TPA A
n = 1 to 5
R = H, alkyl, alkyloxy, -(OCH$_2$CH$_2$)nOG;
G is H or alkyl

TPA B
n = 1 to 5
R = alkyl

TPA C
n = 1 to 3,
R = H, CN, alkyl, alkyloxy,
R' = alkyl, alkyloxyphenyl, phenyl, phenyl(OCH$_2$CH$_2$)nOG;
G is H or alkyl TPA D
n = 1 to 5,
R' = alkyl, alkyloxyphenyl, phenyl(OCH$_2$CH$_2$)nOG;
G is H or alkyl TPA E
n = 1 to 5,
R = H, alkyl, and -(OCH2CH2)nOG;
G is H or alkyl,
R' = alkyl

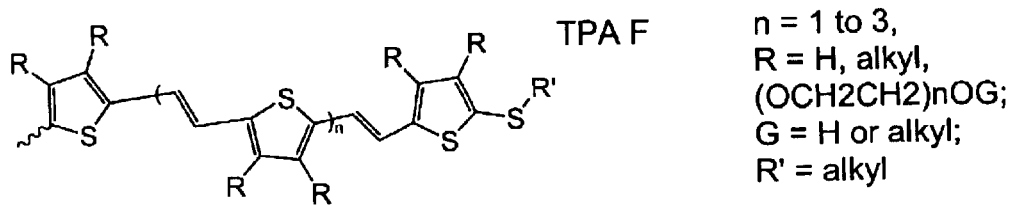
TPA F
n = 1 to 3,
R = H, alkyl, (OCH2CH2)nOG;
G = H or alkyl;
R' = alkyl
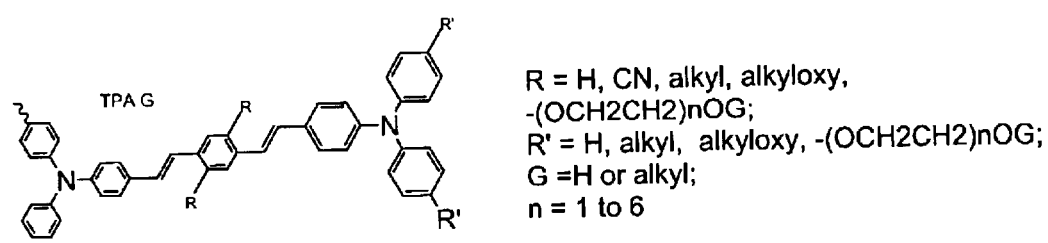
TPA G
R = H, CN, alkyl, alkyloxy, -(OCH2CH2)nOG;
R' = H, alkyl, alkyloxy, -(OCH2CH2)nOG;
G = H or alkyl;
n = 1 to 6
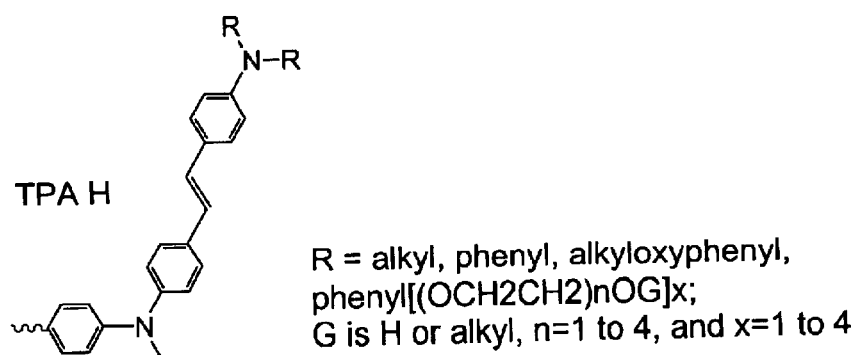
TPA H
R = alkyl, phenyl, alkyloxyphenyl, phenyl[(OCH2CH2)nOG]x;
G is H or alkyl, n=1 to 4, and x=1 to 4
For TPA's A to H,
"alkyl" = $C_1$ to $C_{20}$ alkyl
Figure 6, page 2

Formation of (diphenylamino)-substituted aldehydes, Wittig reagents 4',4"-bis(diphenylamino)stilbene and 4',4"-bis(diphenylamino)diphenyl-1,3-butadiene.

Formation of α,ω-bis-(diphenylamino)diphenylpolyenes.

Formation of α,ω-bis-(dialkylamino)diphenylpolyenes.

Formation of α,ω-bis-(diphenylamino)-PPV-dimer and α,ω-(dialkylamino)-PPV-dimer.

Formation of diphenylamino), N'-ethyl. N'-(2"-hydroxyethyl)amino-diphenylpolyenes.

I. = n-BuLi/TMEDA/THF; S;
II. = Ac₂O/pyridine
III. = POCl₃/DMF
IV.
V.

Formation of substituted dithienylpolyenes.

Formation of substituted PTV oligomers

Preparation of dithienylpolyene precursors.

Preparation of dithienylpolyenes.

Derivatization and functionalization of terminal Aryl rings for Porphyrin attachment.

Derivatization and Functionalization of terminal Thienyl rings for Porphyrin Attachment.

PORPHYRINS WITH ENHANCED MULTI-PHOTON ABSORPTION CROSS-SECTIONS FOR PHOTODYNAMIC THERAPY

This application claims priority under 35 U.S.C. § 119 to U.S. Provisional Patent Application No. 60/313,815 filed on Aug. 22, 2001, and to U.S. Provisional Patent Application No. 60/348,393 filed on Jan. 16, 2002, the disclosures of which are hereby incorporated by reference in their entireties.

BACKGROUND OF THE INVENTION

1. Field of the Invention

This invention relates to porphyrin-based compounds modified with a chromophore useful in photodynamic therapy ("PDT"), particularly multi-photon PDT, and methods of using the compounds in PDT and related applications. In particular, a method of treating a tumor disease or a tumor by contacting an therapeutically effective amount of the porphyrin-based compound and irradiating the modified porphyrin with sufficient radiation to produce singlet oxygen is disclosed. Preferably the modified porphyrin simultaneously absorbs two photons of radiation which radiation is preferably is in a range of about 700 nm to about 1300 nm.

2. Discussion of the Related Art

Photodynamic therapy is an accepted treatment of tumors, as well as age related macular degeneration. PDT is initiated by introducing a photosensitizer agent into a subject's blood stream. After an appropriate time interval (usually tens of hours), the photosensitizer is activated by shining a visible light, usually a red color laser beam, at the tumor's location.

PDT employs the special ability of some porphyrin and porphyrin-like photosensitizers to accumulate in pathologic cells, and to transfer, upon or subsequent to radiation, absorbed photon energy to naturally occurring oxygen molecules in blood and tissue. Photophysical processes constituting PDT using porphyrins agents are summarized in the energy level diagram shown in FIG. 1.

In its classical implementation, absorption of one photon of visible wavelength takes a photosensitizer molecule into a short-lived excited state, $S_1$, with energy of 170–190 kJ mol$^{-1}$, which corresponds to an illumination wavelength of about 620 to 690 nm. After a few nanoseconds, the porphyrin converts into a triplet state, $T_1$, by an intersystem crossing (ISC) mechanism with energy of 110–130 kJ mol$^{-1}$ and a much longer lifetime, on the order of milliseconds. From this triplet state, energy is transferred to omnipresent oxygen molecules by switching them from a triplet ground state, $3\Sigma g$, into an excited singlet state, $1\Delta g$, which has an excitation energy of 94 kJ mol–1. Once in the excited singlet state, the oxygen presents an extremely active species, which reacts chemically with the surrounding cell material and causes tumor apoptosis.

The use of longer wavelength, near-infrared, light to cause absorption of two photons of longer wavelength light has been developed to treat breast and other cancers. See U.S. Pat. Nos. 5,829,448, 5,832,931, 5,998,597, and 6,042,603. This two-photon technique employs a mode-locked Ti:sapphire laser to administer PDT with near-infrared light. In contrast to one-photon PDT, the near-infrared light produced by the Ti:sapphire laser is at a wavelength substantially longer than the characteristic one-photon absorption waveband of the photoreactive agent employed. Instead of the single photon absorption process involved in a conventional photodynamic reaction, a two photon process may occur upon radiation with a pulse of the 700–1300 nm light.

Due to its relatively long wavelength, the near-infrared light emitted by a Ti:sapphire laser can penetrate into tissue up to 8 centimeter or more, making it possible to treat tumors that are relatively deep within a subject's body, well below the dermal layer.

For photosensitizer molecules to be particularly efficacious they should selectively accumulate in the tumor tissue. It is known that porphyrin-based molecules possess this feature. To date, the U.S. Food and Drug Administration has approved at least two porphyrin-based PDT agents: Photofrin®, and Verteporfrin®. Photofrin® is a naturally occurring porphyrin, which absorbs light in the visible spectral range ($\lambda$<690 nm). However, neither of these compounds have significant absorption spectra in the near-infrared region of radiation of 700 to 1300 nm, nor do they exhibit efficient multi-photon absorption.

Chemical modification of the porphyrin structure, such as to chlorin or bacteriochlorin, to shift the one-photon absorption band to longer wavelengths is limited by the fundamental requirement that the energy of the $T_1$ state be higher than the excitation energy of singlet oxygen. Furthermore, such structural modification of the porphyrin structure may result in a less stable compound.

Non-porphyrin-based materials may have enhanced TPA cross-sections but typically lack either the ability to generate singlet oxygen, or have either unknown or deleterious interaction properties with biological tissue.

Thus, there is a need of porphyrin-based materials which safely interact with biological tissue and exhibit both a significant two-photon absorption cross-section for radiation in the near-infrared region and the ability to generate singlet oxygen. There is also a need to effectively treat tumors and other manifestations of disease located deep within a subject's body by PDT. Presently known and approved PDT agents require the use of radiation ranging from about 620 nm to 690 nm. This range of radiation typically penetrates most tissues to a depth of no more than a few millimeters.

SUMMARY OF THE INVENTION

The invention meets the need to treat physical manifestations of diseases or disorders located within a subject's body with photodynamic therapy by providing porphyrin-based compounds which undergo simultaneous two photon absorption (TPA) upon exposure to radiation easily transmitted by a subject's tissue to produce, in due course, singlet oxygen. The use of radiation in the tissue transmission region permits the treatment of disorders located more than a few millimeters within a subject's body.

In one embodiment, the invention relates to porphyrin-based compounds modified with chromophores to provide enhanced multi-photon absorption of radiation in the range of about 700 nm to about 1300 nm. One or more of the chromophores may be attached to the porphyrin ring at any one of the 2, 3, 5, 7, 8, 10, 12, 13, 15, 17, 18 or 20 positions, that is, at either one of the "beta" or "meso" positions of the porphyrin. The chromophores may be directly attached to the ring structure or there may be a linking structure between the porphyrin ring and the chromophore. The inventive compounds may also be based on various reduced forms of porphyrin, such as, for example, chlorin (2,3-dihydroporphyrin), bacteriochlorin (7,8,17,18-tetrahydroporphyrin), and isobacteriochlorin.

In another general embodiment, the invention is directed to a method for generating singlet oxygen by irradiating a porphyrin-based compound with multiple photons, generally two photons, of near-infrared radiation. The compound may comprise a porphyrin-based compound substituted with one or more chromophores at the beta or meso positions, and further substituted with an intersystem crossing enhancing substituent also at the beta or meso positions.

Another general embodiment of the invention is further directed to a method of treating a tumor disease or a tumor by contacting an therapeutically effective amount of a porphyrin-based compound modified with one or more chromophores and at least one intersystem crossing enhancing substituent as set forth herein and irradiating the modified porphyrin with sufficient radiation to produce singlet oxygen. Preferably, the modified porphyrin absorbs two photons of radiation which radiation is preferably is in a range of about 700 nm to about 1300 nm.

In another embodiment, the invention relates to a pharmaceutical use of the inventive porphyrin compound in an amount that is therapeutically effective for the treatment of tumors or other disorders.

In yet another embodiment, the invention is directed to a method of increasing the multi-photon absorption cross-section of a porphyrin-based photosensitizer by attaching at least one TPA-chromophore at the meso or beta positions of a porphyrin structure of the porphyrin-based photosensitizer, and also attaching at least one intersystem crossing enhancing substituent to meso or beta positions of a porphyrin structure of the porphyrin-based photosensitizer. These attachments result in an increased multi-photon absorption cross-section of the porphyrin-based photosensitizer and significant ability to generate singlet oxygen. The increased multi-photon absorption cross-section may be at least about 30 GM units, preferably at least about 50 GM units, and more preferably at least about 70 GM units. The absorption cross-section is measured at about the photosensitizer's maximum wavelength for two-photon absorption.

A further embodiment of the invention may include a porphyrin-based compound comprising the following porphyrin structure:

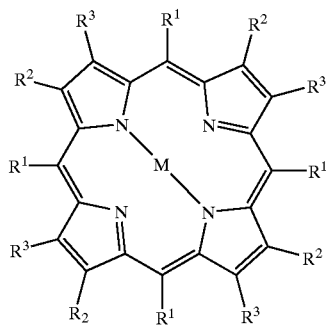

wherein each $R^1$ is independently -L-TPA, —H, —Ar, —(CH$_2$)$_n$CH$_3$, —CH═CH$_2$, —(CH$_2$O)$_n$-G, -t-Butyl, or —C(O)OG; each $R^2$ is independently -L-TPA, —H, —Ar, —(CH$_2$)$_n$CH$_3$, —CH═CH$_2$, —(CH$_2$O)$_n$-G, -t-Butyl, or —C(O)OG; each $R^3$ is independently -L-TPA, —H, —Ar, —(CH$_2$)$_n$CH$_3$, —CH═CH$_2$, —(CH$_2$O)$_n$-G, -t-Butyl, or —C(O)OG; or independently $R^2$ and $R^3$ are linked by —C$_4$H$_4$— to form a six-membered ring; M is either two hydrogen atoms or a metal ion; each n is independently an integer ranging from 1 to 20; each G is independently —H, or a C$_1$ to C$_{20}$ alkyl; Ar comprises one of C$_6$H$_5$, C$_6$H$_4$X, C$_6$H$_3$X$_2$, C$_6$H$_2$X$_3$, C$_6$HX$_4$, or C$_6$X$_5$, wherein X comprises one of F, Cl, Br, or I; L is a linking moiety between the porphyrin structure and TPA; TPA is a chromophore moiety; and wherein at least one of $R^1$, $R^2$ or $R^3$ is a L-TPA moiety, and at least one other of $R^1$, $R^2$ or $R^3$ is not H or a L-TPA moiety.

Preferably, the TPA chromophore moiety may be attached to the porphyrin ring directly or with a linking group L. The linking group may be selected from the group consisting of ethenyl, ethynyl, —(CH$_2$)$_n$— wherein n is equal to 1 to 20, ortho-phenyl, meta-phenyl, para-phenyl, —C(═O)—O—, and 4-phenyl-2'-ethenyl.

The TPA-chromophore may be any of the following structures:

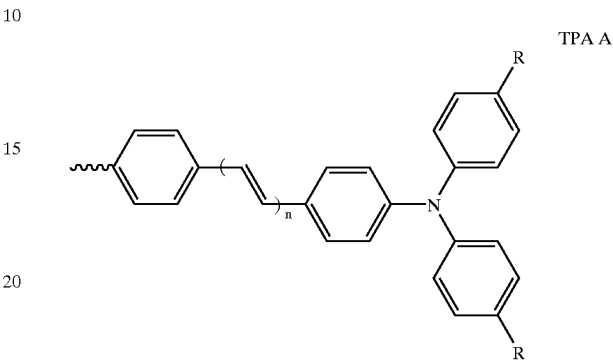

TPA A wherein in TPA A, n=1 to 5, and R comprises one member selected from the group consisting of H, alkyl, alkyloxy, —(OCH$_2$CH$_2$)$_n$OG; wherein G is H or alkyl;

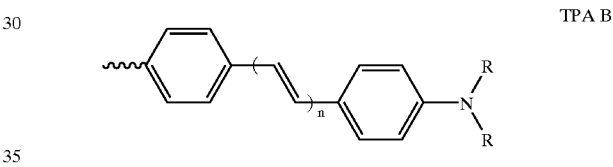

TPA B wherein in TPA B, n=1 to 5, and R comprises an alkyl;

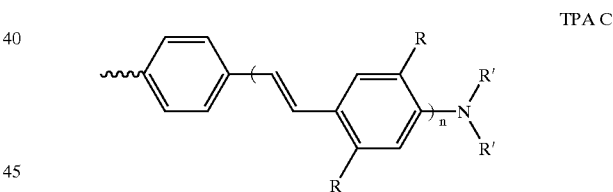

TPA C wherein in TPA C, n=1 to 3, R comprises one member selected from the group consisting of H, CN, alkyl, alkyloxy, and R' comprises one member selected from the group consisting of alkyl, alkyloxyphenyl, phenyl, phenyl-(OCH$_2$CH$_2$)$_n$OG; wherein G is H or alkyl;

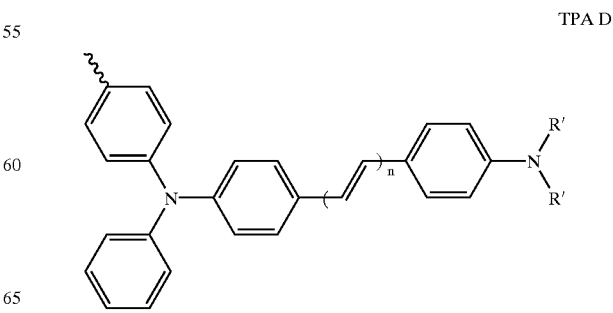

TPA D wherein in TPA D, n=1 to 5, and R' comprises one member selected from the group consisting of alkyl, alkyloxyphenyl, phenyl-$(OCH_2CH_2)_nOG$; wherein G is H or alkyl;

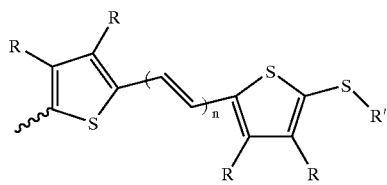

TPA E wherein in TPA E, n=1 to 5, R comprises one member selected from the group consisting of H, alkyl, and —$(OCH_2CH_2)_nOG$; wherein G is H or alkyl, and R' comprises alkyl;

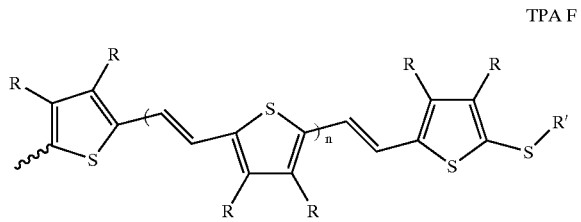

TPA F wherein in TPA F, n=1 to 3, R comprises one member selected from the group consisting of H, alkyl, $(OCH_2CH_2)_n$OG; wherein G is H or alkyl, and R' comprises alkyl;

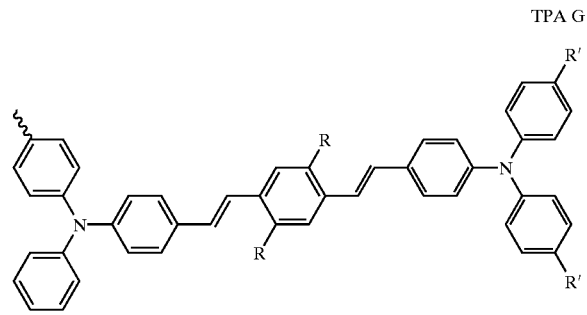

TPA G wherein in TPA G, R comprises one member selected from the group consisting of H, CN, alkyl, alkyloxy, —$(OCH_2CH_2)_nOG$, and R' comprises one member selected from the group consisting of H, alkyl, alkyloxy, —$(OCH_2CH_2)_nOG$; and wherein G is H or alkyl and n=1 to 6;

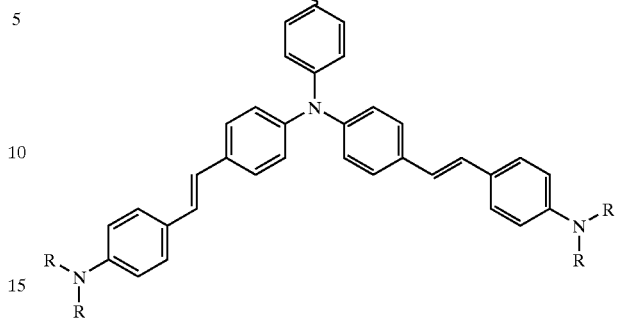

TPA H wherein in TPA H, R comprises one member selected from the group consisting of alkyl, phenyl, alkyloxyphenyl, phenyl[$(OCH_2CH_2)_nOG]_x$; wherein G is H or alkyl, n=1 to 4, and x=1 to 4; wherein in TPA's A to H, alkyl comprises $C_1$ to $C_{20}$ alkyl moieties; and wherein the TPA may be attached to the porphyrin ring at the point indicated by the wiggle line ("〰").

The porphyrin structure of the porphyrin-based photosensitizer may be any one of porphyrin, chlorin, bacteriochlorin, and isobacteriochlorin. The porphyrin-based photosensitizer may absorb two photons of radiation in the range of about 700 nm to about 1300 nm, preferably the range is about 700 nm to about 1100 nm.

Another embodiment of the invention is improving the method of conducting photodynamic therapy which comprises providing a pharmaceutically effective amount of a photoactive compound to within a subject, contacting the photoactive compound with an area to be treated within a subject, and exposing the area to radiation with a wavelength ranging from between about 700 nm to about 1300. The improvement comprises utilizing as the photosensitizer the porphyrin-based photosensitizer described herein.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings.

(b) The dependence of the $^1\Delta_g \rightarrow {}^3\Sigma_g$ luminescence intensity ($l_A$) on the average illumination intensity, P, of molecular oxygen in an air-saturated toluene solution of compound I.

Figure 5:
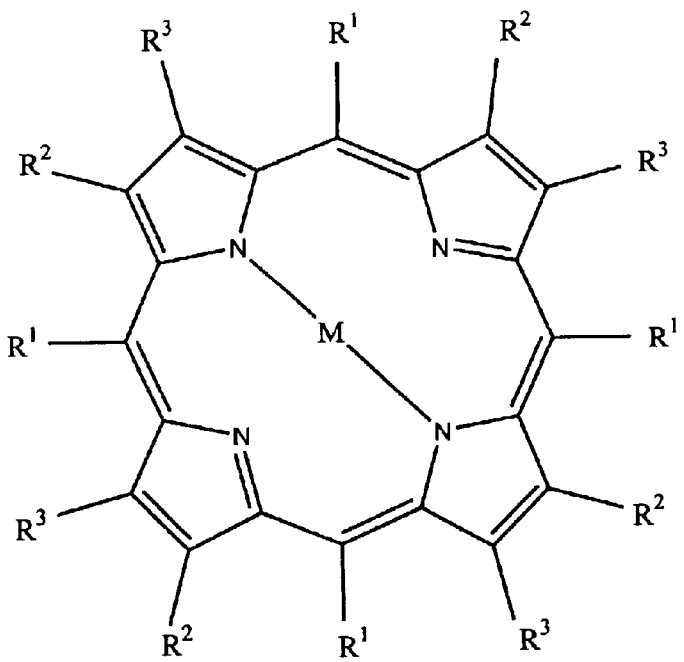

FIG. 5—Porphyrin design motifs for enhancement of their intrinsic two-photon cross-sections.

Figure 6:
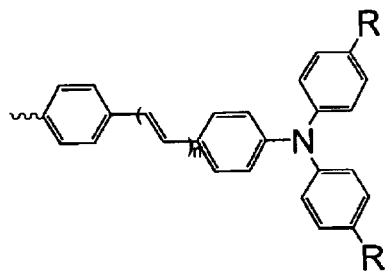
Figure 6:
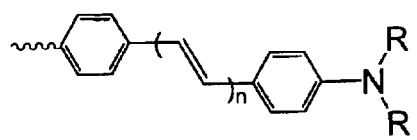
Figure 6:
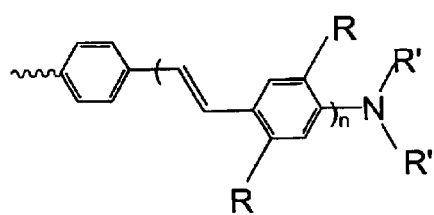
Figure 6:
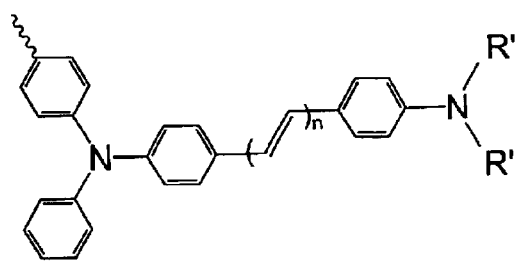
Figure 6:
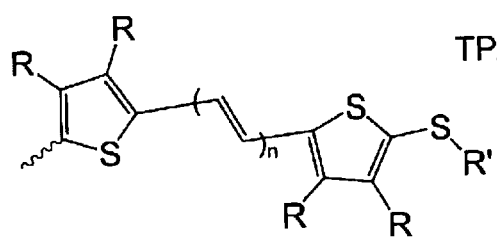

FIG. 6—TPA chromophore motifs with enhanced intrinsic two-photon absorption.

Figure 7:
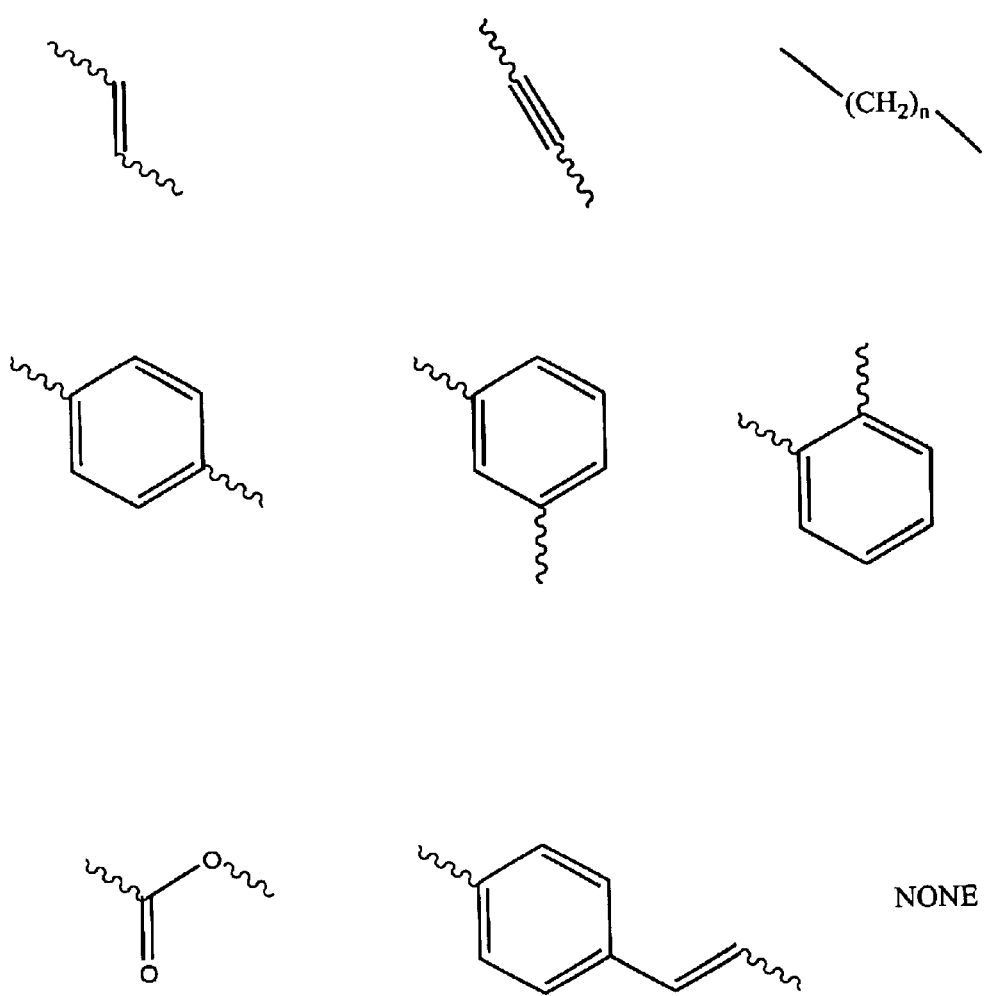

FIG. 7—Linker moieties for attachment of TPA chromophores to porphyrins.

Figure 8:
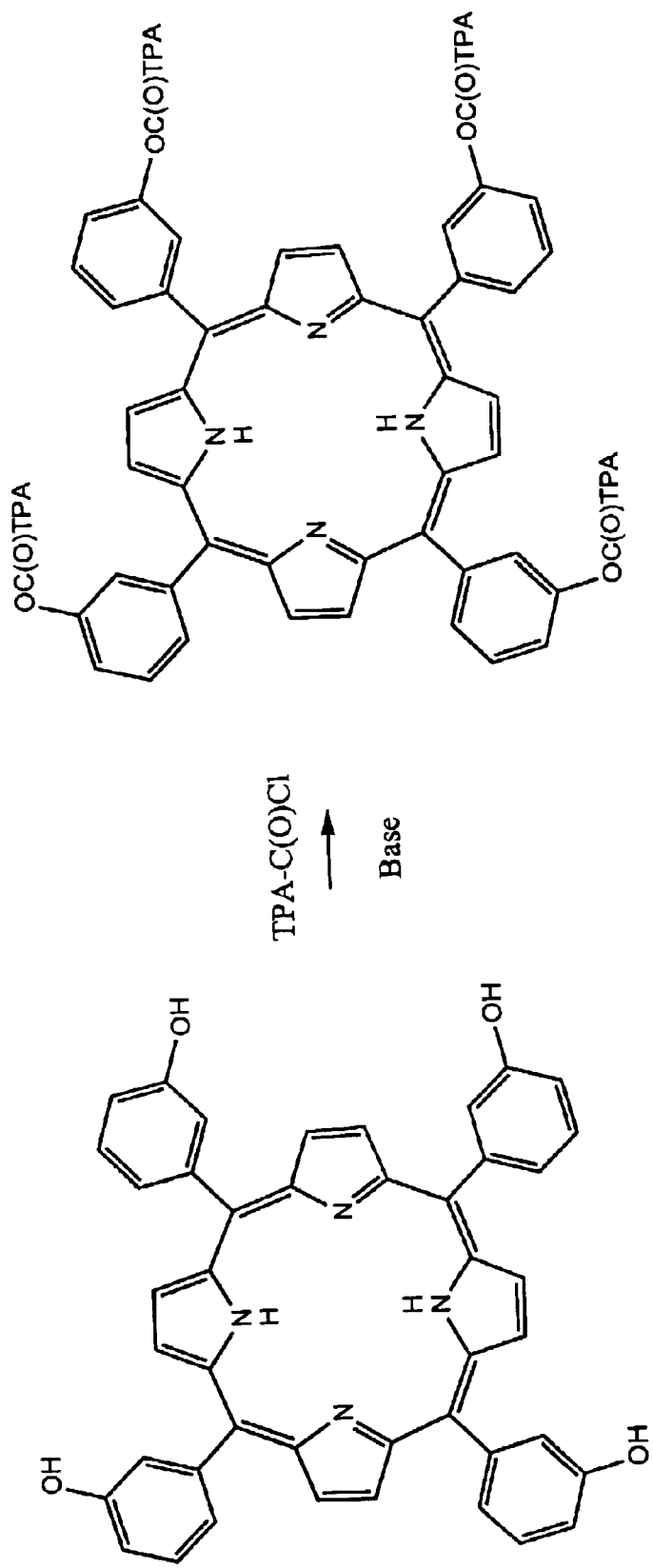

FIG. 8—Conversion of m-THPC to a new derivatized porphyrin with enhanced two-photon absorption.

Figure 9:
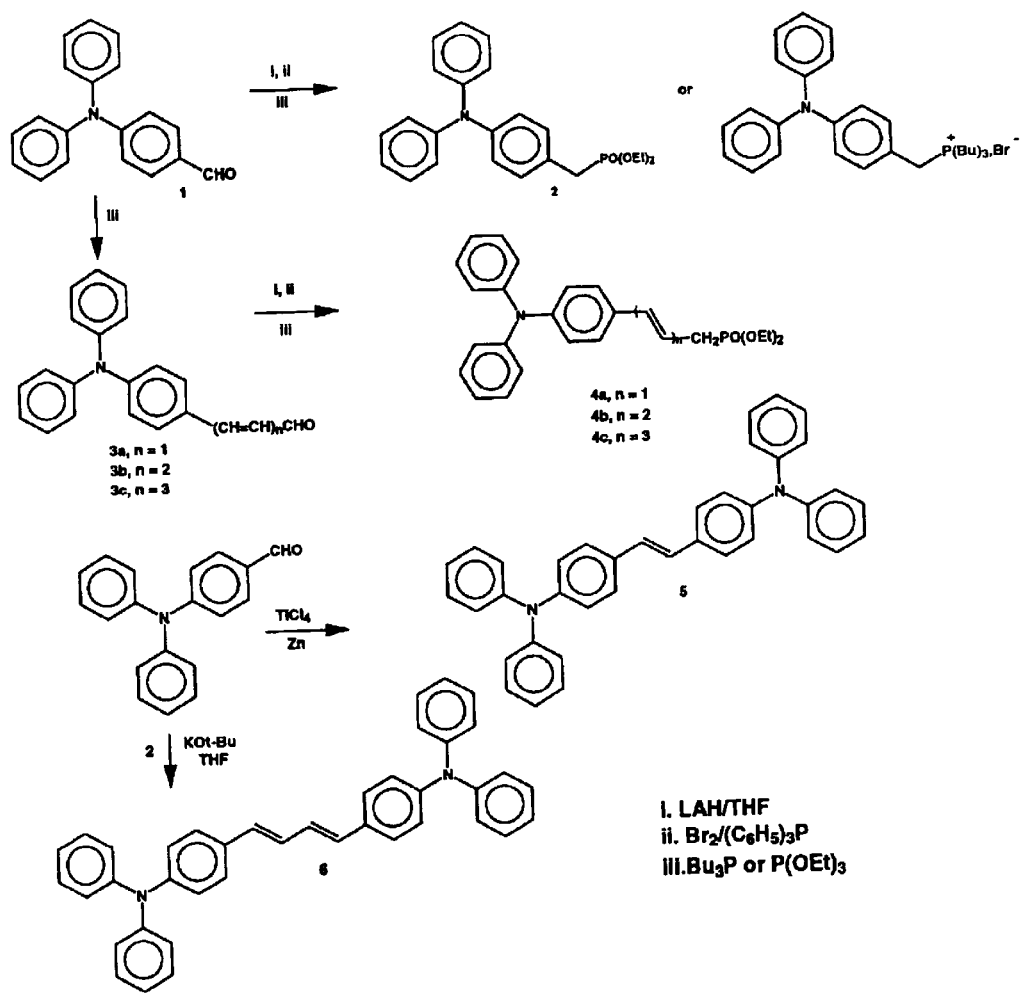
Figure 10:
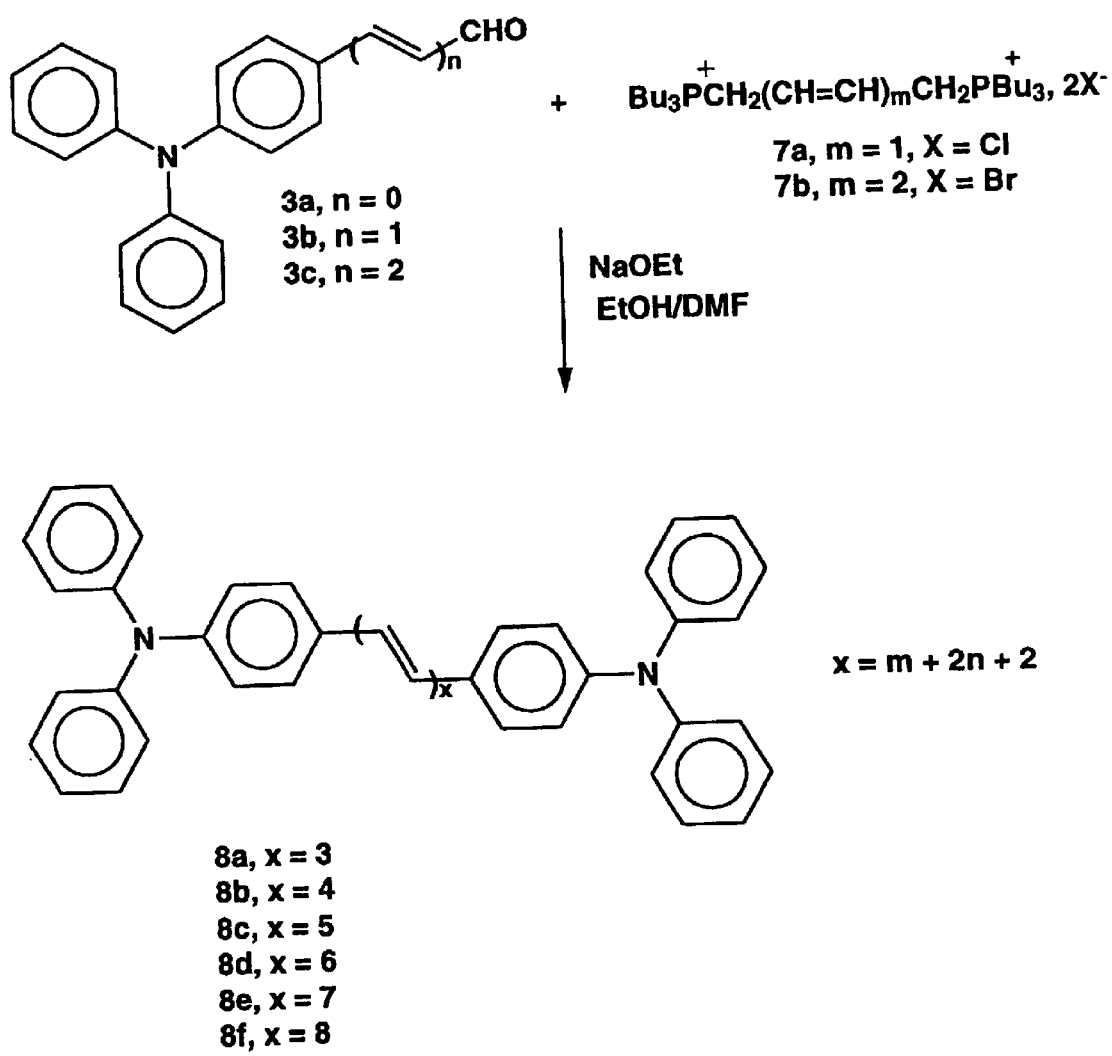
Figure 11:
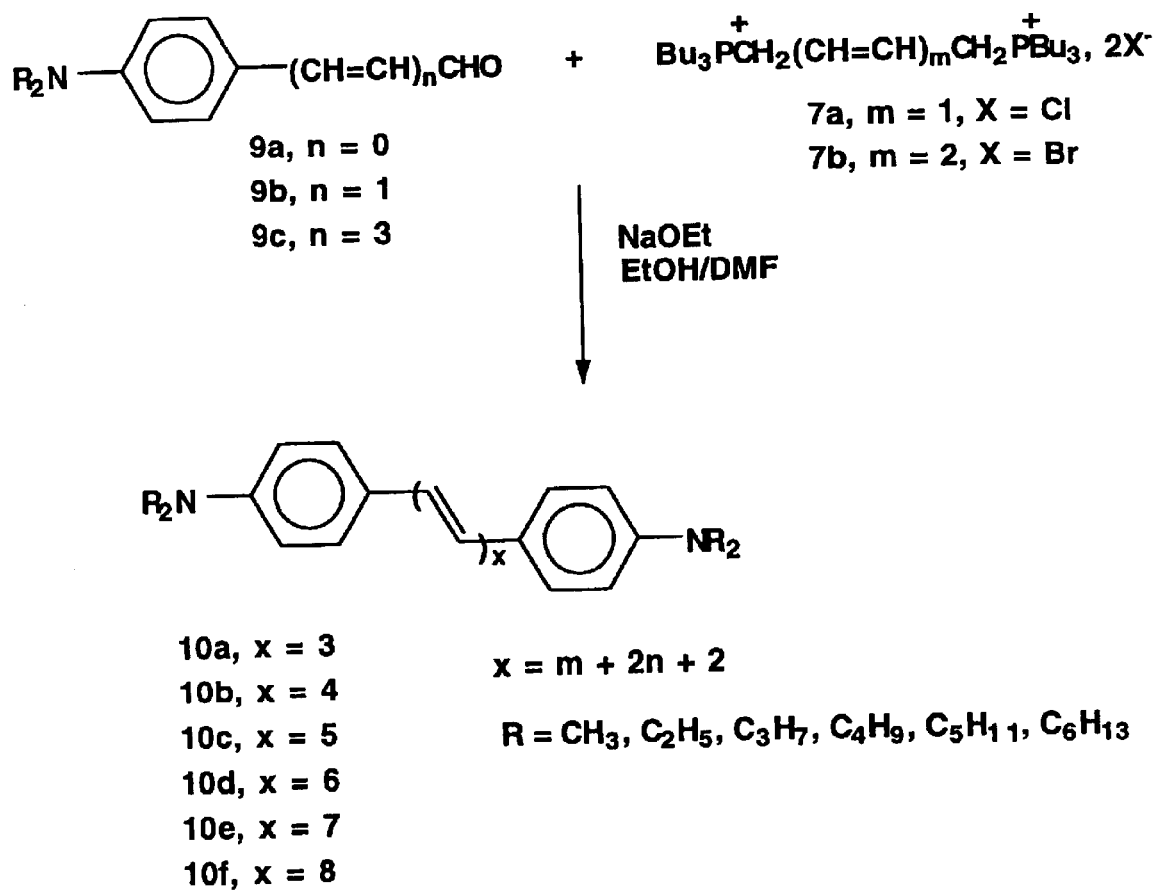
Figure 12:
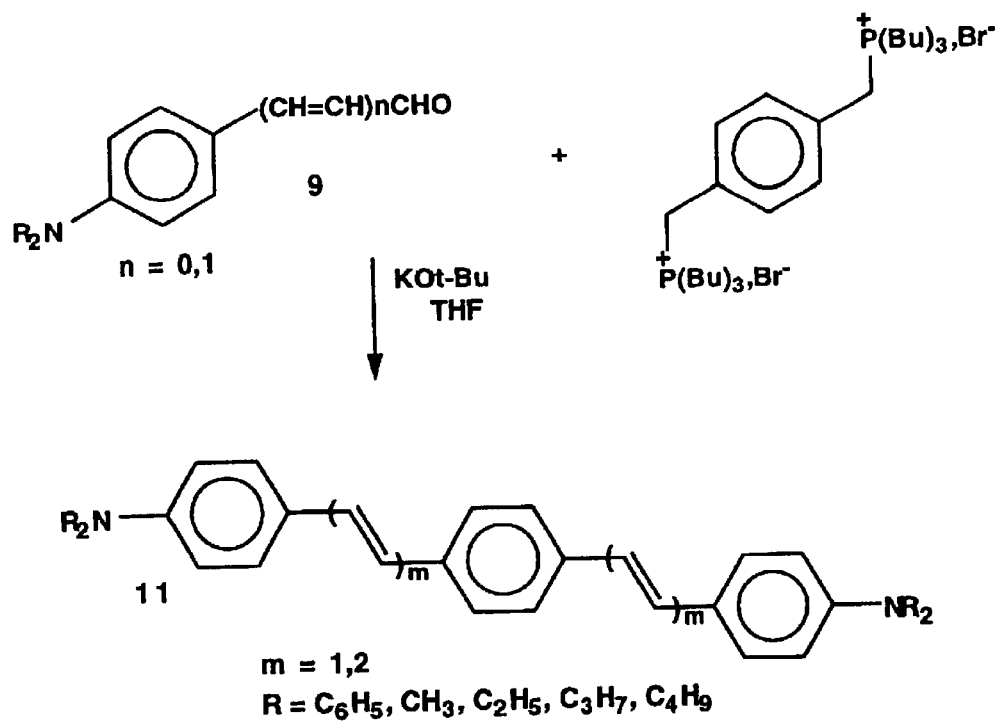

FIG. 9—Scheme showing preparative route for (diphenylamino)-substituted aldehydes FIG. 10—Scheme showing preparative route for α,ω-bis-(diphenylamino)diphenylpolyenes FIG. 11—Scheme showing preparative route for α,ω-bis-(dialkylamino)diphenylpolyenes FIG. 12—Scheme showing preparative route for α,ω-bis-(diphenylamino)-PPV-dimer and α,ω-bis-(dialkylamino)-PPV-dimer (PPV=paraphenylene vinylene)

Figure 13:
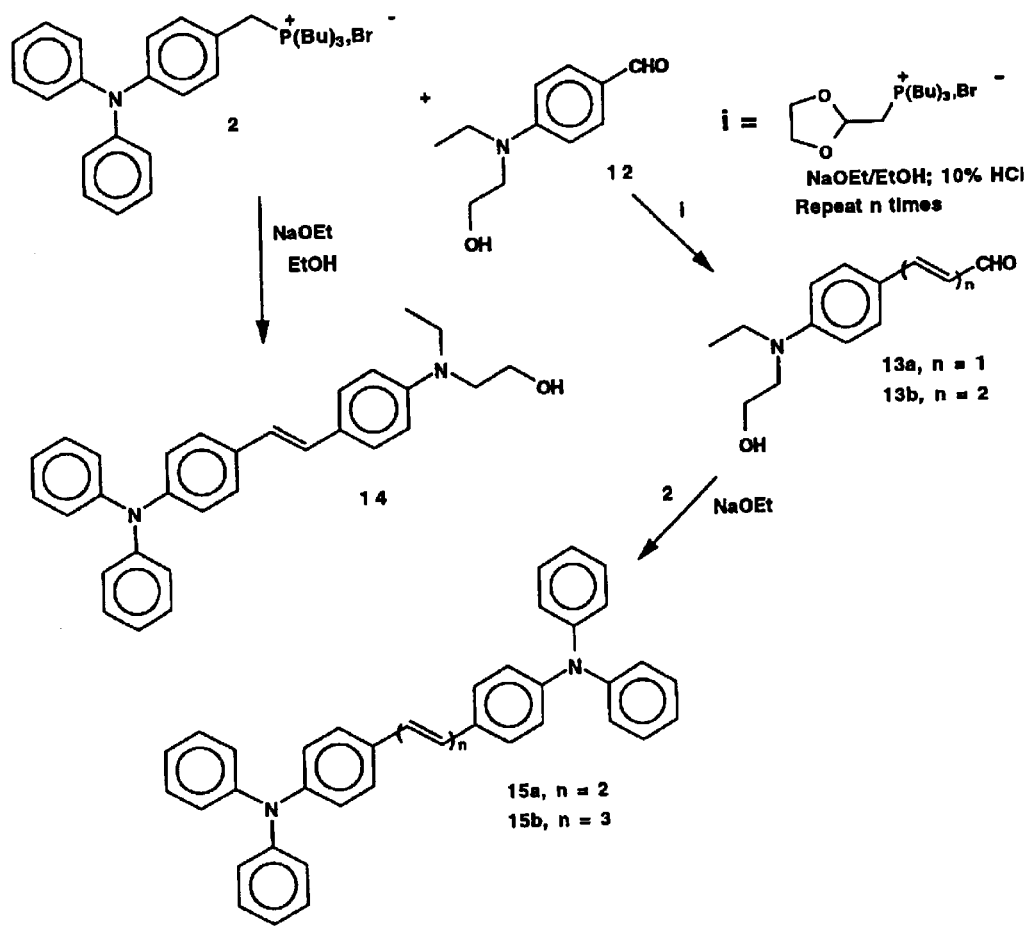

FIG. 13—Scheme showing preparative route for diphenylamino compounds

Figure 14:
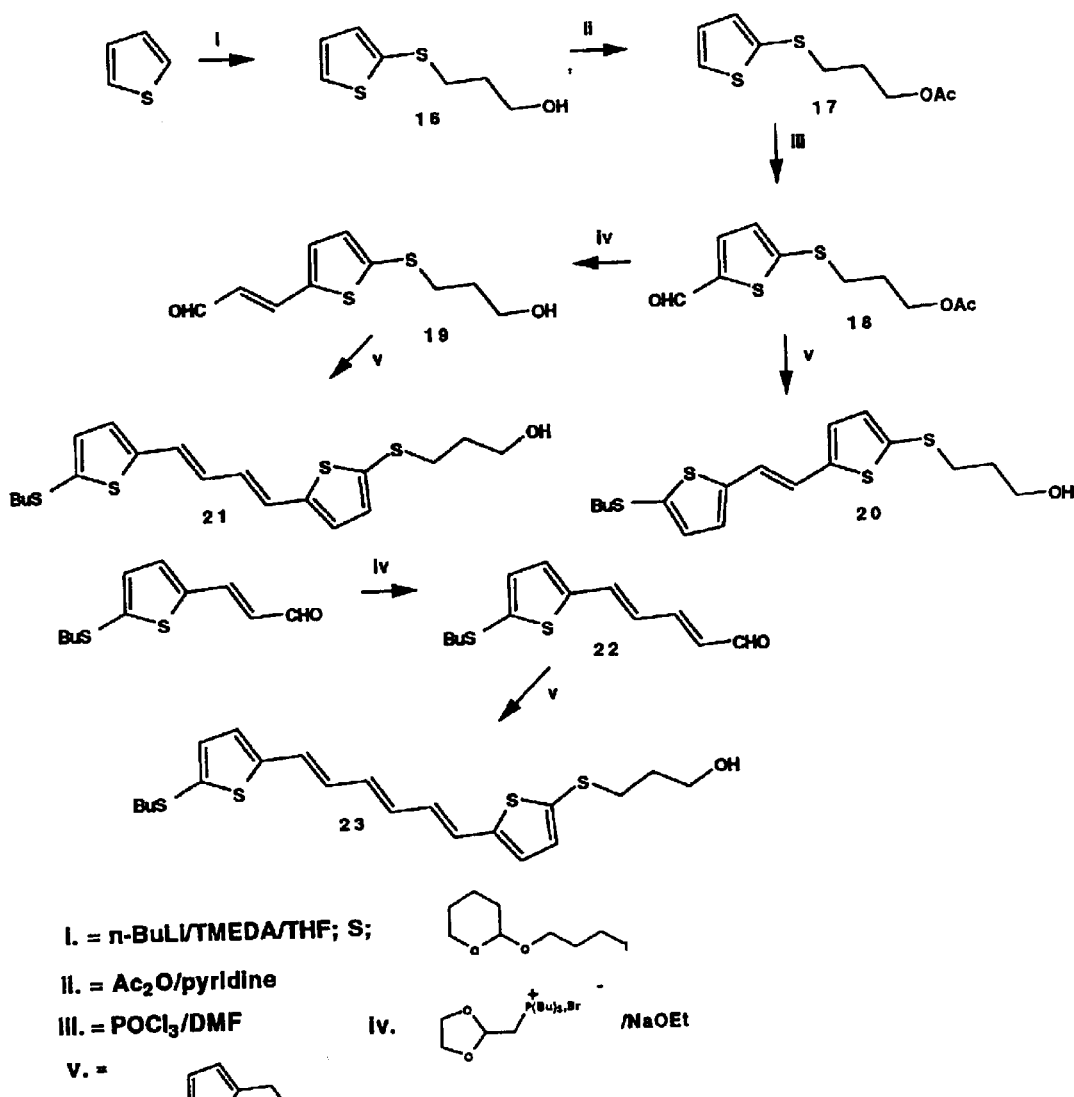

FIG. 14—Scheme showing preparative route for substituted dithienylpolyenes

Figure 15:
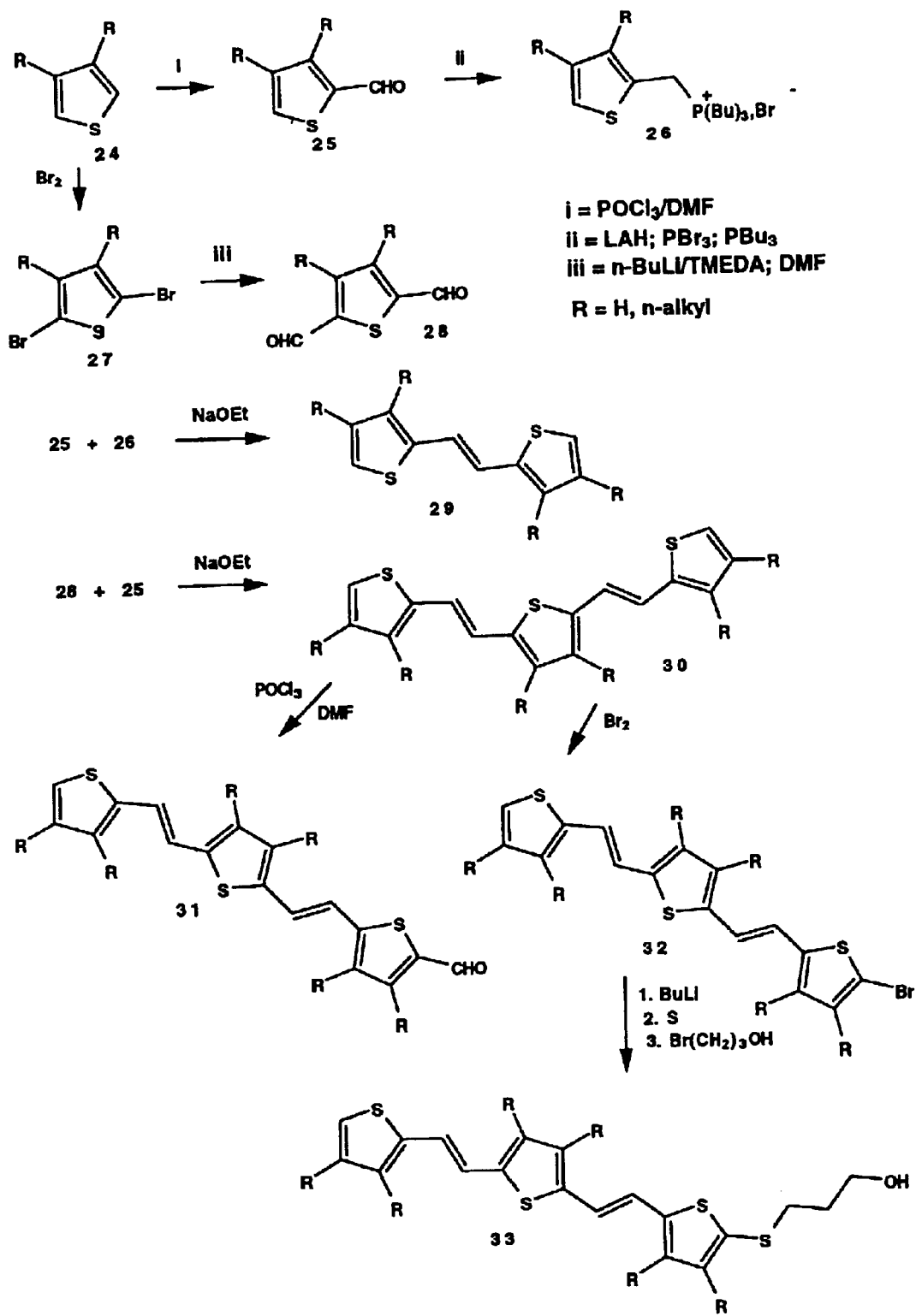

FIG. 15—Scheme showing preparative route for substituted PTV oligomers (PTV=2,5-dithienylene vinylene)

Figure 16:
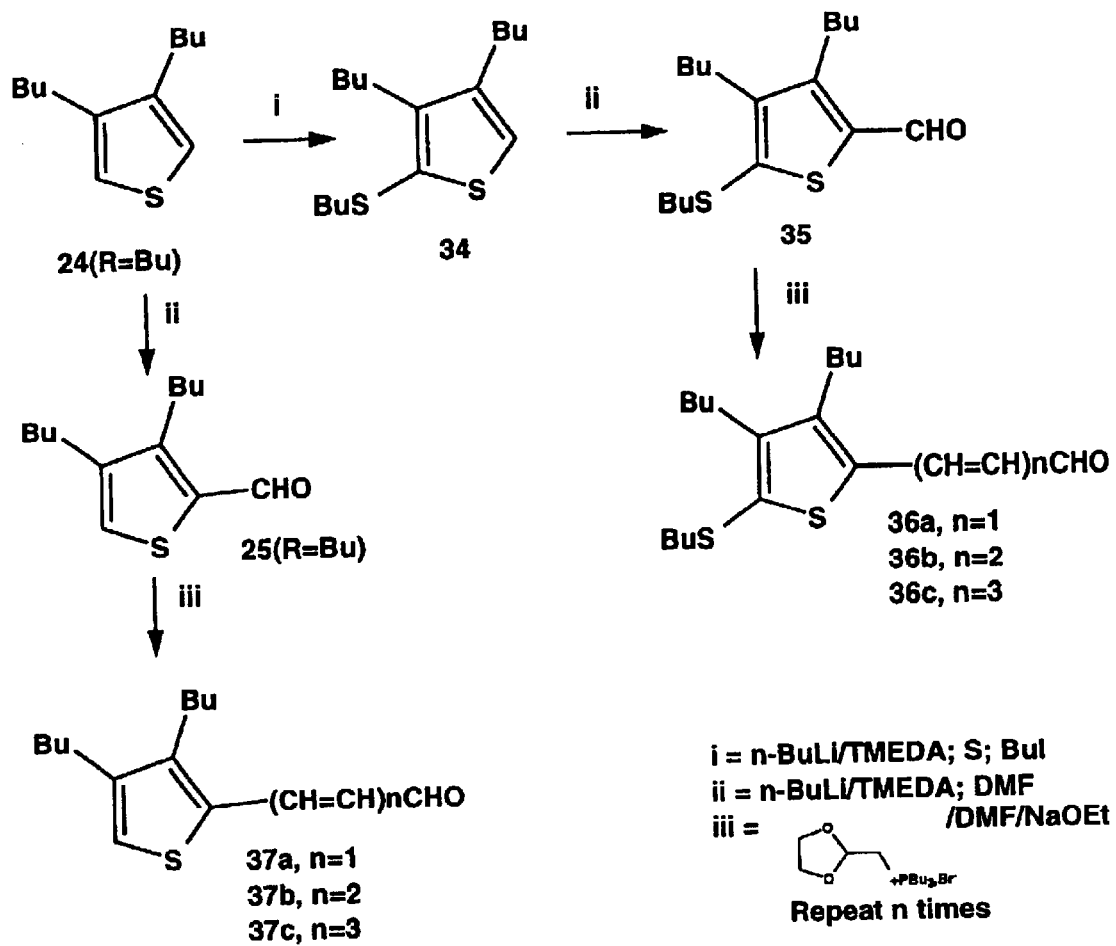

FIG. 16—Scheme showing preparative route for dithienylpolyene precursors

Figure 17:
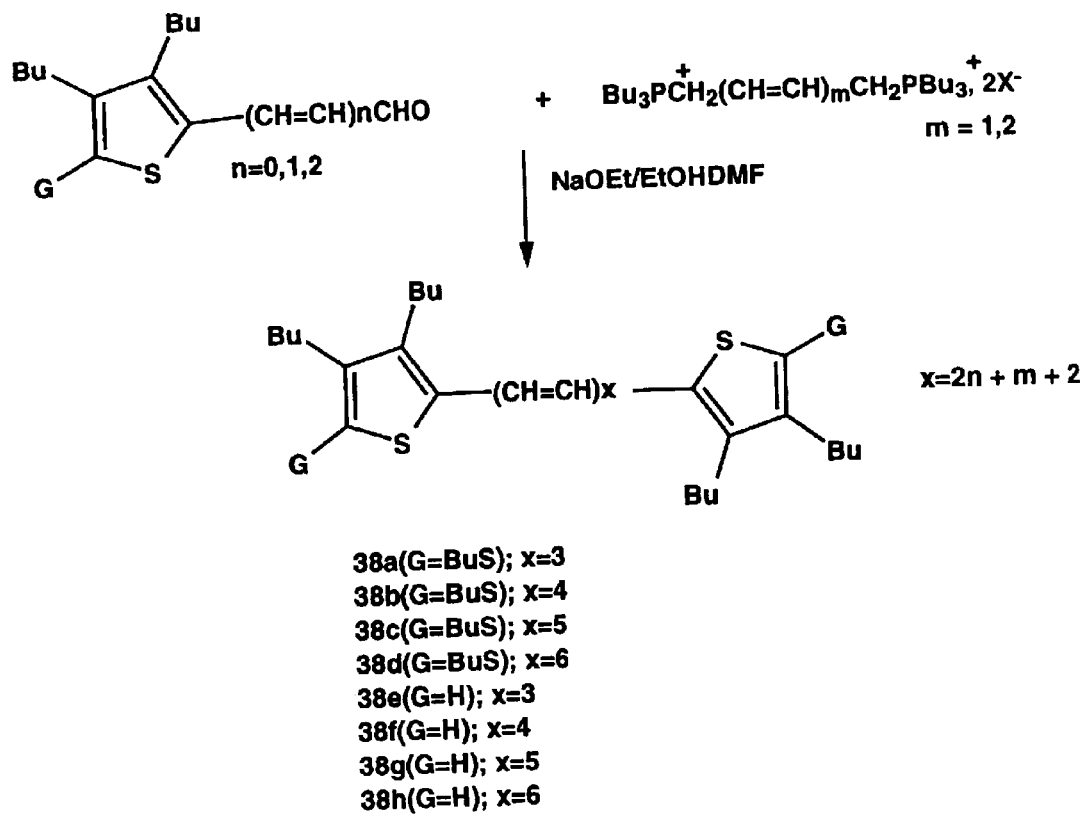

FIG. 17—Scheme showing preparative route for dithienylpolyenes

Figure 18:
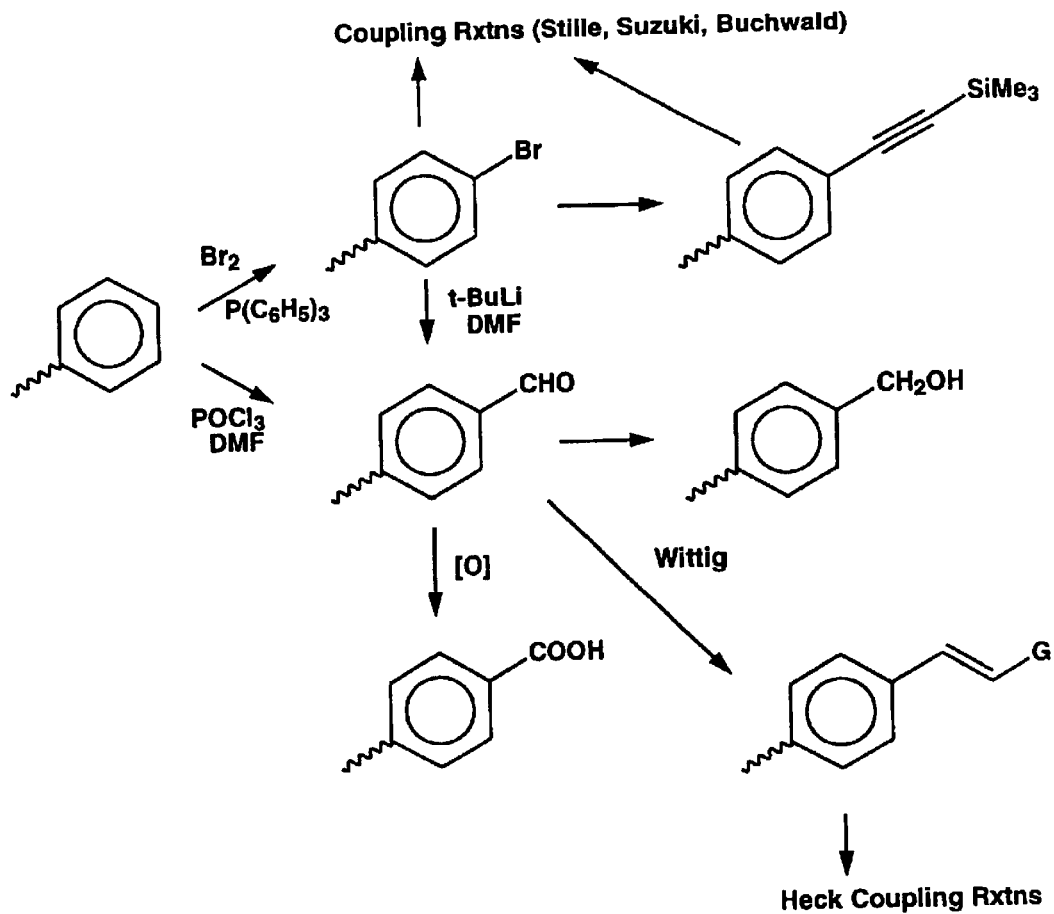
Figure 19:
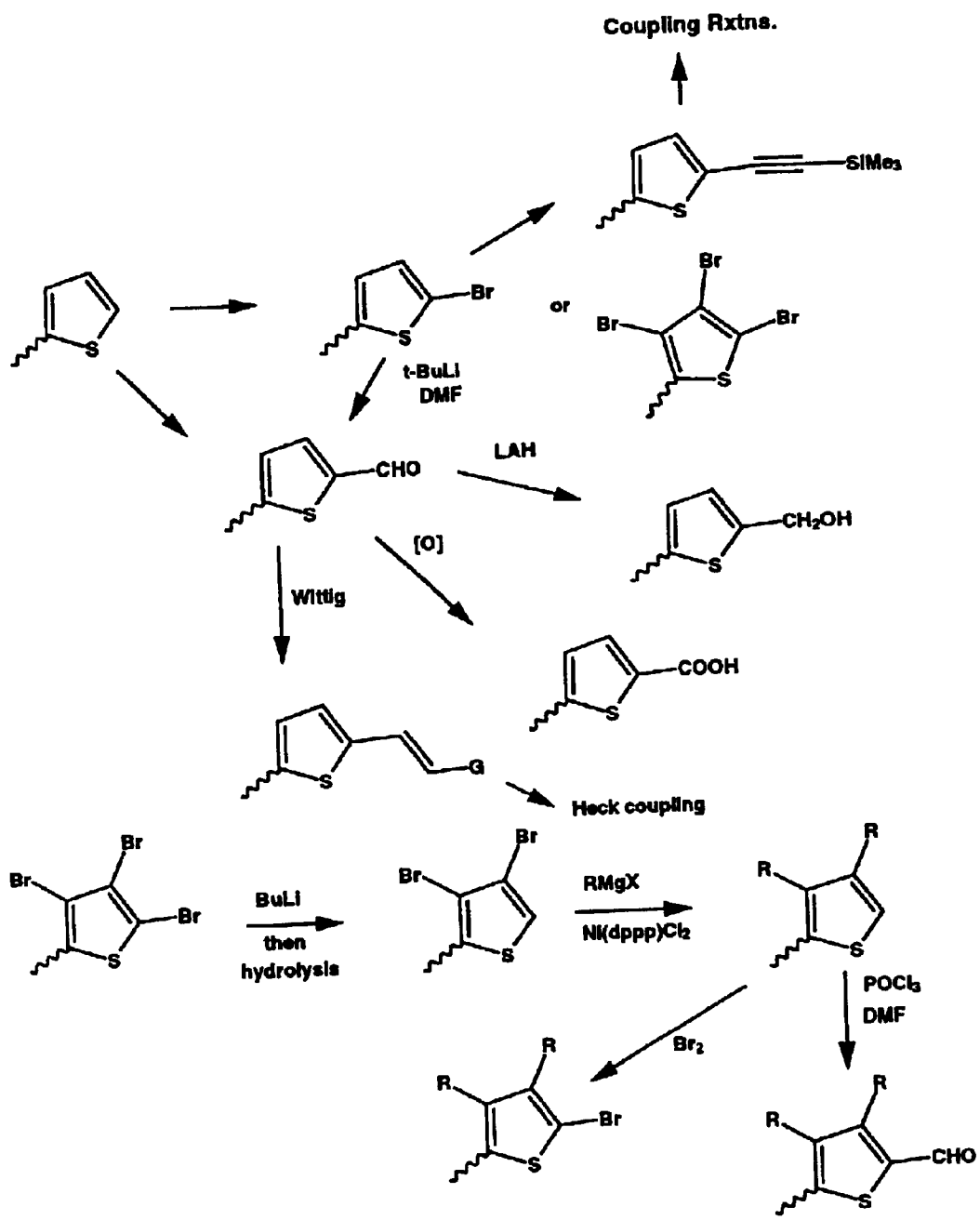
Figure 20:
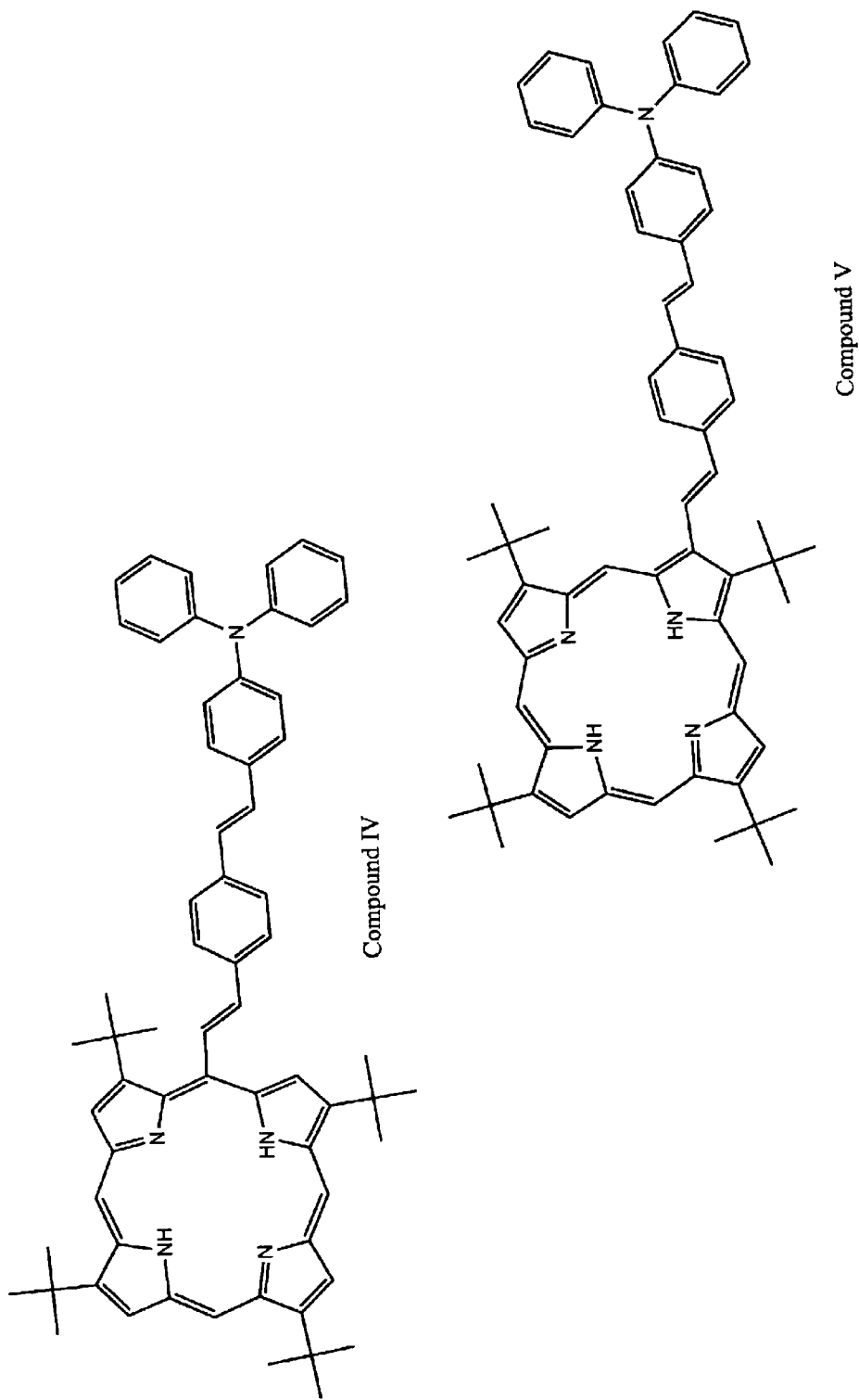

FIG. 18—Scheme showing routes to functionalize terminal aryl rings of chromophores for porphyrin attachment FIG. 19—Scheme showing routes to functionalize terminal thienyl rings of chromophores for porphyrin attachment FIG. 20—Molecular structures of two porphyrins:

Compound IV—5'-[4'''-(diphenylamino)-4''-stilbenyl-1'-ethenyl]-(2,7,12,17-tetra-t-butyl)-21H, 23H-porphyrin; and Compound V—2'-[4'''-(diphenylamino)-4''-stilbenyl-1'-ethenyl]-(3,8,13,18-tetra-t-butyl)-21H, 23H-porphyrin.

DETAILED DESCRIPTION OF THE INVENTION

Figure 1:
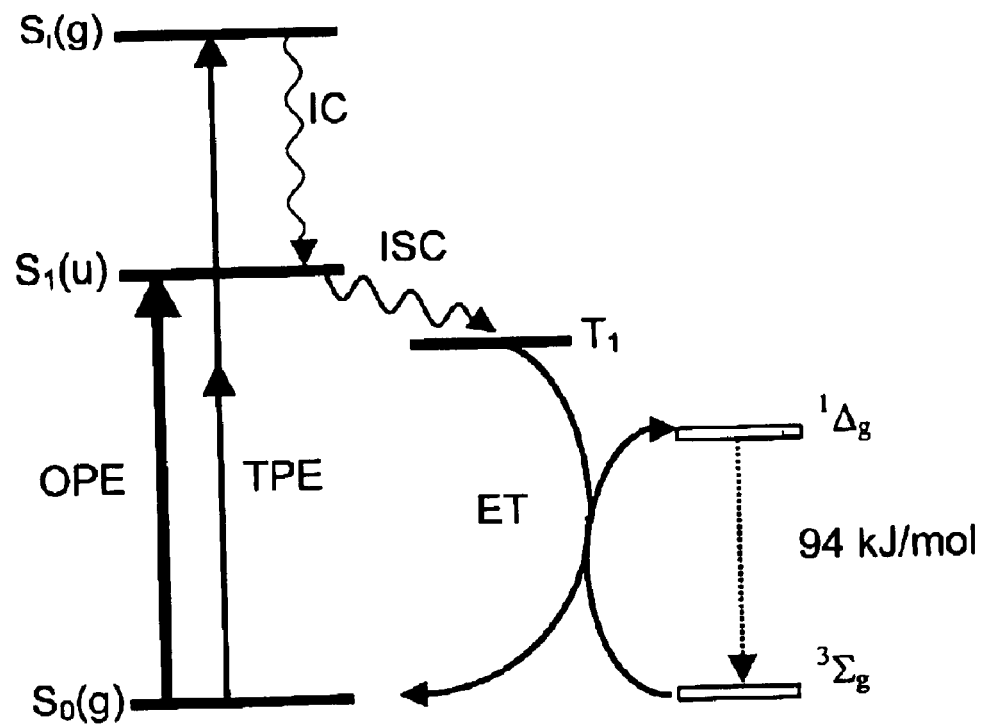
FIG. 1—Schematic of the energy levels for a porphyrin-based photosensitizer (solid bars) and molecular oxygen (open bars).
Figure 2:
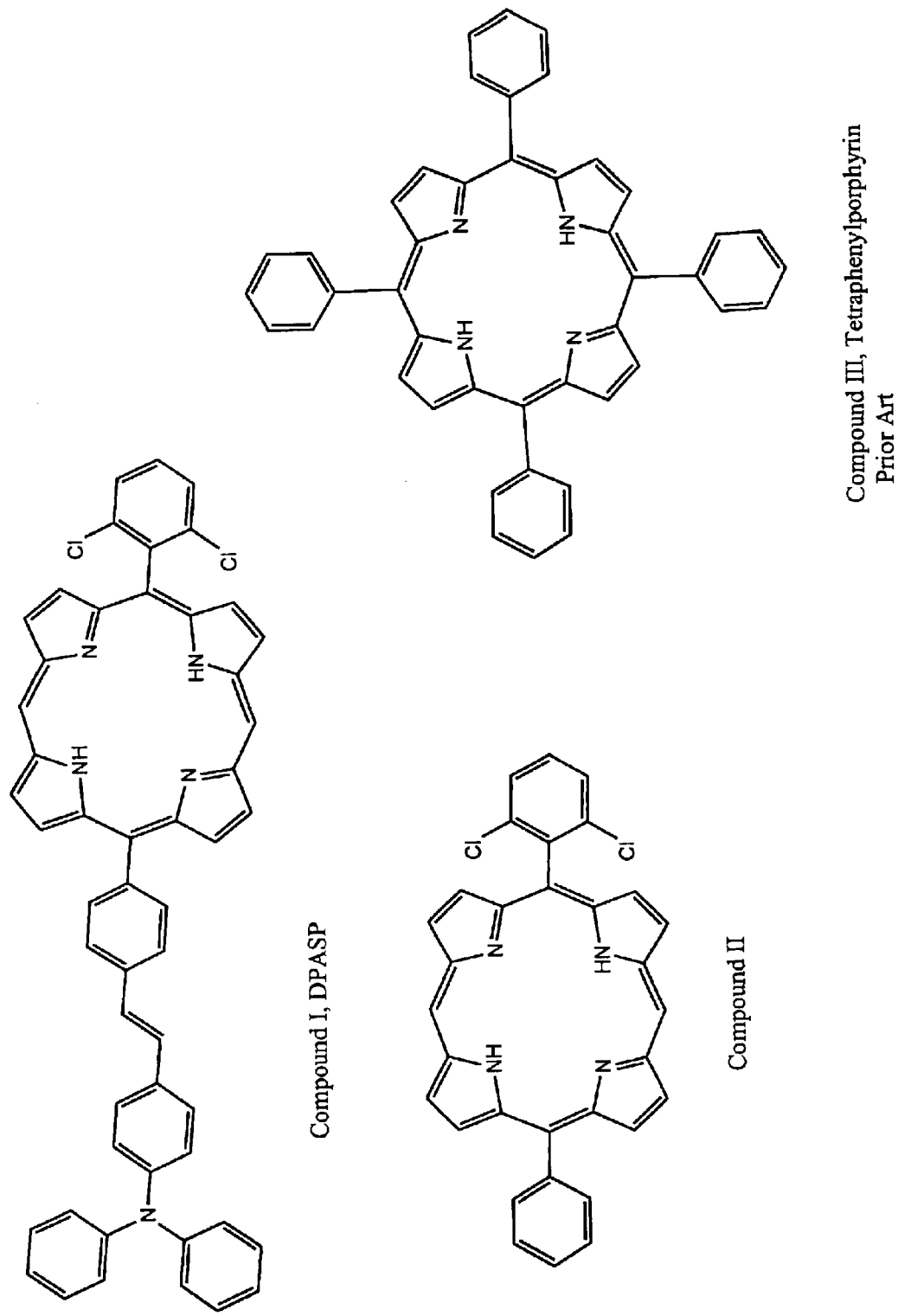
FIG. 2—Molecular structures of three porphyrins:
Compound I—5-[4'''-(diphenylamino)-4''-stilbenyl]-15-[2',6'-dichlorophenyl]-21H, 23H-porphyrin ("DPASP");
Compound II—5-phenyl, 15-(2',6'-dichlorophenyl)-21H, 23H-porphyrin; and
Compound III—5,10,15,20-tetraphenyl-21H,23H-porphyrin.

The energy change associated with photon excitation of a photosensitizer and subsequent energy transfer to produce excited singlet oxygen is represented in FIG. 1. The comparative energy levels for a porphyrin-based photosensitizer and molecular oxygen are represented by solid and open bars, respectively. The ground, first singlet, $i^{th}$ excited singlet, and lowest triplet states of the photosensitizer are labeled $S_0(g)$, $S_1(u)$, $S_i(g)$, and $T_1$, respectively. The symbols in the parentheses denote the gerade (g) and ungerade (u) symmetry of the corresponding states. The ground and the first excited singlet states of molecular oxygen are denoted by $^3\Sigma_g$ and $^1\Delta_g$, respectively.

Upon one-photon excitation ("OPE") the lowest singlet state, $S_1(u)$, of the photosensitizer is populated. Subsequently, the radiationless intersystem crossing ("ISC") $S_1(u) \rightarrow T_1$ takes place. This is followed, in turn, by energy transfer (ET) between the photosensitizer and oxygen; $T_1 + {}^3\Sigma_g \rightarrow S_0(g) + {}^1\Delta_g$ (semicircle arrows). The excited singlet oxygen molecules ($^1\Delta_g$) are detected by their $^1\Delta_g \rightarrow {}^3\Sigma_g$ luminescence at ~1270 nm.

Upon two-photon excitation ("TPE"), a transition occurs to one of the higher excited states $S_i(g)$. In the TPE case the energy of each excitation photon is less than the single excitation photon used in OPE, and the energy of the TPE excitation photon falls into the tissue transparency window. By the internal conversion ("IC") process, the $S_1(u)$ state of the photosensitizer is ultimately populated from the $S_i(g)$ state, and the remaining steps in the process are the same as in the OPE case described above.

Figure 3:
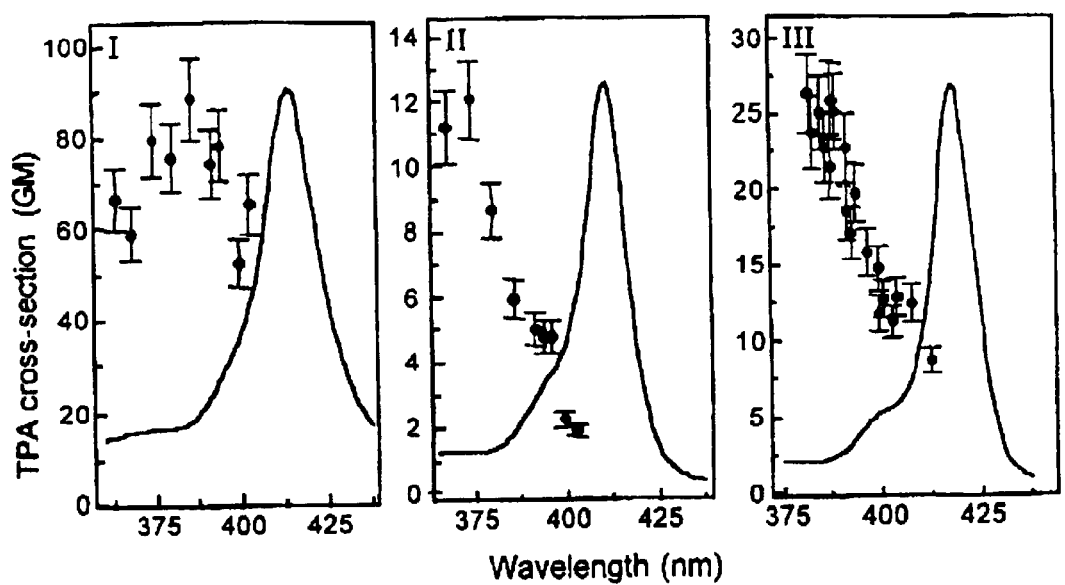
FIG. 3—Two-photon absorption spectra (circles) of $10^{-4}$ M toluene solutions of compounds I, II, and III.

As presented in FIG. 3, the two-photon absorption spectra of compounds I, II, and III could not be measured at wavelengths shorter than about 350 nm because the energy of the excitation photon approaches that of the first excited singlet state $S_1$, and efficient one-photon absorption masks TPA.

FIG. 3 has a horizontal (wavelength) axis corresponding to the transition wavelength, that is, it is half the laser excitation wavelength. The vertical axis shows the TPA cross-sections in Göppert-Mayer units ("GM", 1 GM=$10^{-50}$ cm$^4$ s photon$^{-1}$ molecule$^{-1}$); note the differing scales on the three graphs. The laser system comprised a phase-locked Ti:sapphire regenerative amplifier (Model CPA-1000 made by Clark-MXR, Inc. (Dexter, Mich.)), which was operated at 1 kHz repetition rate and produced 150-fs pulses at 0.6 mJ energy per pulse. These pulses were parametrically down-converted in an optical parametric amplifier ("OPA"), (TOPAS made by Quantronix (East Setanket, N.Y.)) which yielded 100-fs pulses in the range from 1170 to 1640 nm. TPA spectra were obtained by tuning the OPA with subsequent second harmonic generation and registration of the porphyrin fluorescence. Absolute TPA cross-sections were measured by comparing fluorescence intensity under one- and two-photon excitation (see Drobizhev, M., et al. in Chem. Phys. Lett. Vol. 334, pages 76–82 (2001) and references therein for details). Black solid lines represent the appropriately scaled one-photon absorption. All three molecules reveal a characteristic strong Soret band near 415 nm, accompanied by four relatively weak bands in the visible (not shown).

Figure 4:
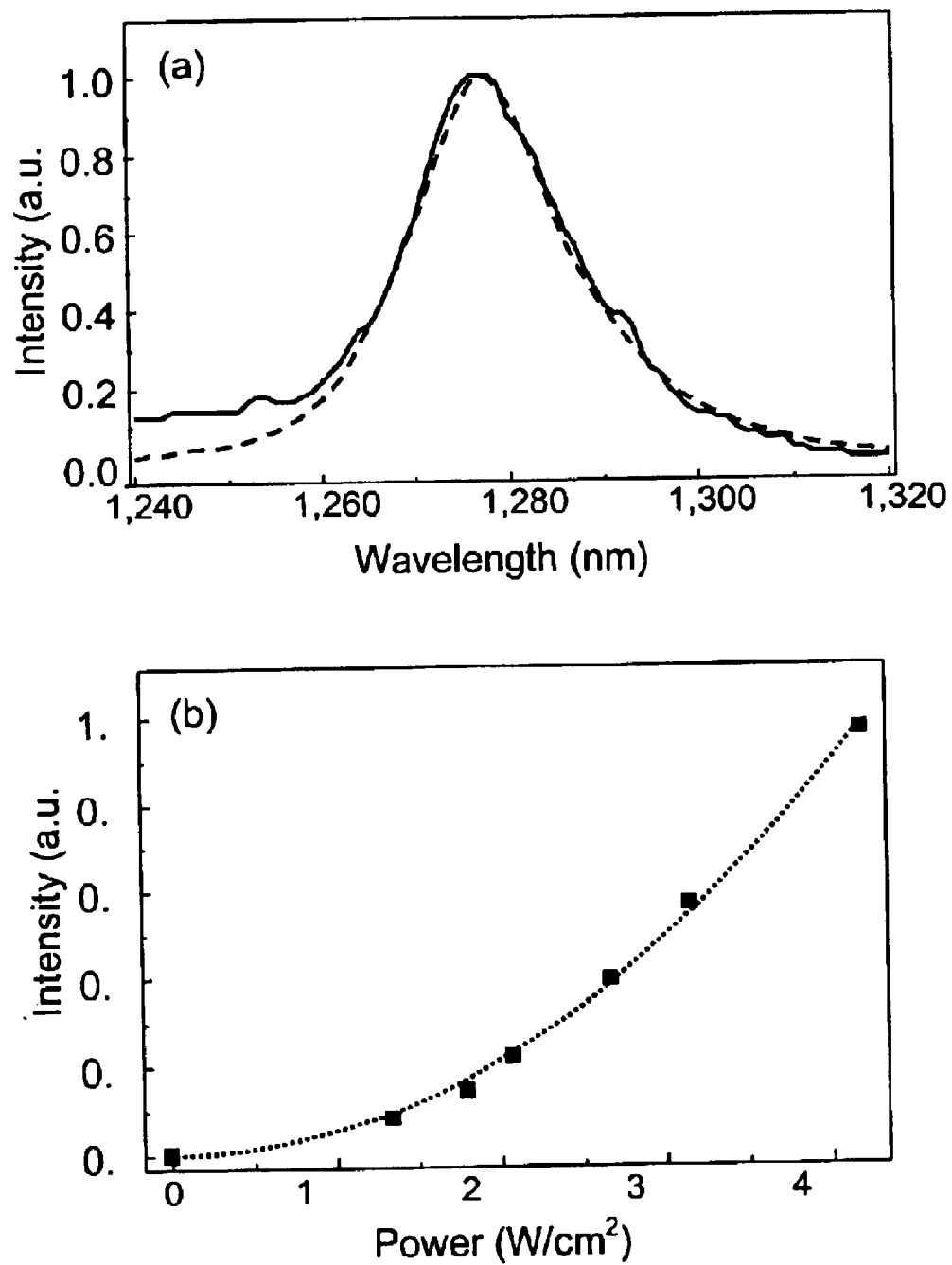
FIG. 4—(a) The $^1\Delta_g \rightarrow {}^3\Sigma_g$ luminescence spectra of molecular oxygen in an air-saturated toluene solution of compound I.

As illustrated in FIG. 4(a), the $^1\Delta_g \rightarrow {}^3\Sigma_g$ luminescence spectra of molecular oxygen in an air-saturated toluene solution of compound I after both one- and two-photon excitation were measured. The one-photon excitation is represented by the dashed line and the two-photon excitation is shown by the solid line. Both spectra are normalized to unity. For one photon excitation, second harmonics of a Ti:sapphire regenerative amplifier, 390 nm, with an average power intensity of 0.5 W/cm$^2$ were used, while for two-photon excitation, the output of a Ti:sapphire regenerative amplifier, 780 nm, with an average power intensity of 15 W/cm$^2$ was used. In both cases, the laser beam was slightly focused into a 1-cm cell to give a cylindrical irradiated volume of ~1.5 mm diameter. The singlet oxygen luminescence spectrum was measured with a nitrogen-cooled Ge detector coupled with Jobin-Yvon monochromator and a lock-in amplifier.

FIG. 4(b) graphs the dependence of the $^1\Delta_g \rightarrow {}^3\Sigma_g$ luminescence intensity ($l_A$) on the average illumination intensity, P, of molecular oxygen in an air-saturated toluene solution of compound I after two-photon excitation. The raw experimental data are shown by black squares, with the best power-law fit, $l_A = aP^n$ with n=2.1±0.1 shown by the dotted line. These results confirm the two photon nature of singlet oxygen production.

The present invention is directed to a method of increasing the multi-photon absorption cross-section of a porphyrin-based photosensitizer by attaching at least one TPA-chromophore at the meso or beta positions of a porphyrin structure of the porphyrin-based photosensitizer, and attaching at least one intersystem crossing enhancing substituent to meso or beta positions of a porphyrin structure of the porphyrin-based photosensitizer.

This modification of the porphyrin photosensitizer increases the multi-photon absorption cross-section of the porphyrin-based photosensitizer to at least about 30 GM units at about its maximum wavelength for two-photon absorption.

The TPA-chromophore may be selected from the following structures:

TPA A

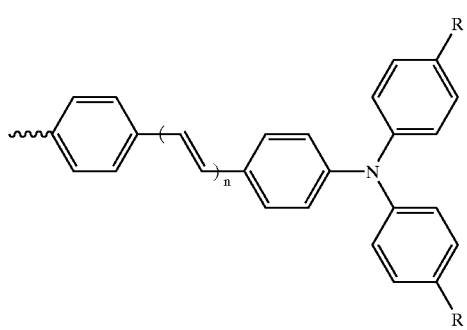

wherein in TPA A, n=1 to 5, and R comprises one member selected from the group consisting of H, alkyl, alkyloxy, —(OCH$_2$CH$_2$)$_n$OG; wherein G is H or alkyl;

TPA B

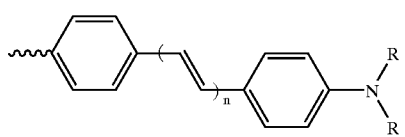

wherein in TPA B, n=1 to 5, and R comprises an alkyl;

TPA C

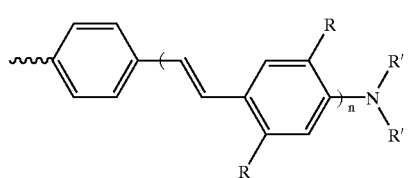

wherein in TPA C, n=1 to 3, R comprises one member selected from the group consisting of H, CN, alkyl, alkyloxy, and R' comprises one member selected from the group consisting of alkyl, alkyloxyphenyl, phenyl, phenyl-(OCH$_2$CH$_2$)$_n$OG; wherein G is H or alkyl;

TPA D

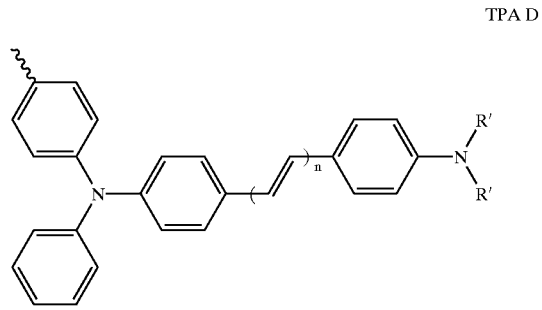

wherein in TPA D, n=1 to 5, and R' comprises one member selected from the group consisting of alkyl, alkyloxyphenyl, phenyl-(OCH$_2$CH$_2$)$_n$OG; wherein G is H or alkyl;

TPA E

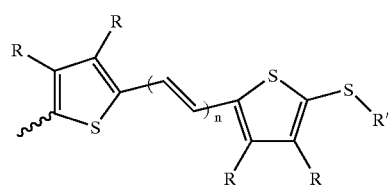

wherein in TPA E, n=1 to 5, R comprises one member selected from the group consisting of H, alkyl, and —(OCH$_2$CH$_2$)$_n$OG; wherein G is H or alkyl, and R' comprises alkyl;

TPA F

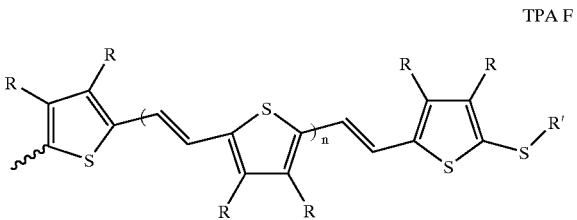

wherein in TPA F, n=1 to 3, R comprises one member selected from the group consisting of H, alkyl, (OCH$_2$CH$_2$)$_n$OG; wherein G is H or alkyl, and R' comprises alkyl;

TPA G

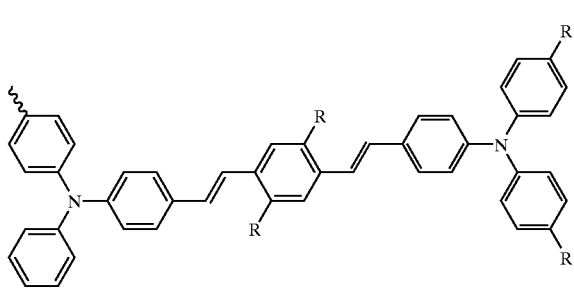

wherein in TPA G, R comprises one member selected from the group consisting of H, CN, alkyl, alkyloxy, —(OCH$_2$CH$_2$)$_n$OG, and R' comprises one member selected from the group consisting of H, alkyl, alkyloxy, —(OCH$_2$CH$_2$)$_n$OG; and wherein G is H or alkyl and n=1 to 6;

TPA H

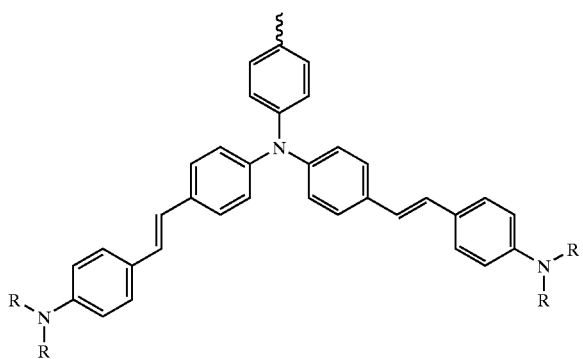

wherein in TPA H, R comprises one member selected from the group consisting of alkyl, phenyl, alkyloxyphenyl, phenyl[(OCH$_2$CH$_2$)$_n$OG]$_x$; wherein G is H or alkyl, n=1 to 4, and x=1 to 4. For TPA's A to H, alkyl comprises C$_1$ to C$_{20}$ alkyl moieties; and the TPA is attached to the porphyrin ring at the point indicated by the wiggle line ("∿∿").

The TPA-chromophore may be attached directly to the porphyrin ring or via a linking group. The linking group may be any one of ethenyl, ethynyl, —(CH$_2$)$_n$— wherein n is equal to 1 to 20, ortho-phenyl, meta-phenyl, para-phenyl, —C(=O)—O—, and 4-phenyl-2'-ethenyl.

Without limiting the invention, the present theory regarding the generation of singlet oxygen, as illustrated in FIG. 1, involves an intersystem crossing step. A photosensitizer's ability to generate singlet oxygen appears to be significantly influenced by the ease at which it undergoes the intersystem crossing step. This ability may be enhanced by the addition of ISC enhancing substituents to the porphyrin ring.

These intersystem crossing enhancing substituents include the group consisting of C$_6$H$_5$, C$_6$H$_4$X, C$_6$H$_3$X$_2$, C$_6$H$_2$X$_3$, C$_6$HX$_4$, or C$_6$X$_5$, wherein X may be one of F, Cl, Br, or I. The halogens may be substituted onto the phenyl ring in any combination of halogens and ring positions.

The porphyrin ring is the preferred ring structure for the photosensitizer but reduced porphyrin forms, such as, chlorin, bacteriochlorin, and isobacteriochlorin, may be utilized as the basic ring structure for the photosensitizer.

Preferably, the porphyrin-based photosensitizer absorbs two photons of radiation in the range of about 700 nm to about 1300 nm, more preferably the absorbed radiation is in a range of about 700 nm to about 1100 nm.

The porphyrin-based photosensitizer may be based on the following porphyrin structure:

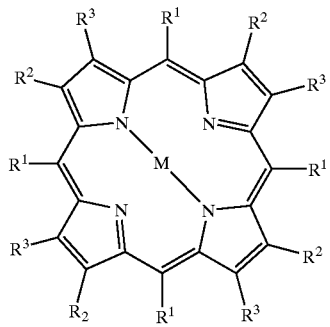

wherein each R$^1$ is independently -L-TPA, —H, —Ar, —(CH$_2$)$_n$CH$_3$, —CH=CH$_2$, —(CH$_2$O)$_n$-G, -t-Butyl, or —C(O)OG; each R$^2$ is independently -L-TPA, —H, —Ar, —(CH$_2$)$_n$CH$_3$, —CH=CH$_2$, —(CH$_2$O)$_n$-G, -t-Butyl, or —C(O)OG; each R$^3$ is independently -L-TPA, —H, —Ar, —(CH$_2$)$_n$CH$_3$, —CH=CH$_2$, —(CH$_2$O)$_n$-G, -t-Butyl, or —C(O)OG; or independently R$^2$ and R$^3$ are linked by —C$_4$H$_4$— to form a six-membered ring; M is either two hydrogen atoms or a metal ion; each n is independently an integer ranging from 1 to 20; and each G is independently —H, or a C$_1$ to C$_{20}$ alkyl.

Ar comprises one of C$_6$H$_5$, C$_6$H$_4$X, C$_6$H$_3$X$_2$, C$_6$H$_2$X$_3$, C$_6$HX$_4$, or C$_6$X$_5$, wherein X comprises one of F, Cl, Br, or I; L is a linking moiety between the porphyrin structure and TPA; and TPA is a chromophore moiety as described above. At least one of the R$^1$, R$^2$ or R$^3$ porphyrin-ring substituents is a L-TPA moiety, while at least one other of R$^1$, R$^2$ or R$^3$ is not H or a L-TPA moiety. Preferably, one of R$^1$, R$^2$ or R$^3$ is an Ar group.

The TPA moiety may be attached to the porphyrin ring directly or with a linking group, L. The linking group may be one of ethenyl, ethynyl, —(CH$_2$)$_n$— wherein n is equal to 1 to 20, ortho-phenyl, meta-phenyl, para-phenyl, —C(=O)—O—, and 4-phenyl-2'-ethenyl. Most preferably, the compound may be 5-[4'''-(diphenylamino)-4''-stilbenyl]-15-[2', 6'-dichlorophenyl]-21H, 23H-porphyrin.

Additionally, M may be any metal atom. Preferred are metals which are biologically acceptable to a subject's body without deleterious health effects. Alternatively, M may be two hydrogen atoms.

The compounds described herein may be advantageously utilized as PDT agents in the treatment of tumors or other physical manifestations of a disease or condition. Such a use would be an improvement over the PDT treatments and agents presently known, by allowing the effective use of treatment radiation with a wavelength ranging from between about 700 nm to about 1300 nm, radiation which easily passes through living tissue to produce singlet oxygen. Preferably, the PDT agent absorbs two photons of radiation in a range of about 700 nm to about 1100 nm.

An improved treatment method calling for the pharmaceutical use of the inventive porphyrin compound in an amount that is therapeutically effective for the treatment of tumors or other disorders with an improved two photon absorption cross-section at about its maxima for two-photon absorption is another application of the compounds. A therapeutically effective amount of the compound would range from about 0.1 mg to about 10 mg per kg of body weight of the subject.

The chromophores and porphyrin with the chromophores attached may be prepared by following the general synthetic procedures outlined in FIGS. 9 to 19. Specifically, preparative routes for amino-containing chromophores are outlined in FIGS. 9 to 13, while thienyl-containing chromophore preparative routes are set forth in FIGS. 14 to 17. Methods of functionalizing the terminal aryl or thienyl group of the chromophores for subsequent attachment to the porphyrin ring at the desired position or positions by means of general coupling reactions are set forth in FIGS. 18 to 19.

EXPERIMENTAL DETAILS

The solvents and reagents used were obtained from Fisher Scientific and Aldrich Chemical Companies and used as received.

Compound II was prepared via the same preparative route as set forth for compound I below. Compounds I and II are purified by flash chromatography on silica using 20–40% dichloromethane/hexane gradient. Molecular structures were confirmed by spectroscopic analysis. Compound III was purchased from Aldrich and used as received.

EXAMPLE 1

5-[4'''-(diphenylamino)-4''-stilbenyl]-15-[2',6'-dichlorophenyl]-21H, 23H-porphyrin (Compound I)

Trifluoroacetic acid (17.2 µL, 0.22 mmol) was added to a mixture of 10-(2,6-dichlorophenyl)bilane (100 mg, 0.15 mmol) and 4'-diphenylaminostilbene-4''-carbaldehyde (83.6 mg, 0.15 mmol) in dichloromethane (23 mL) at RT under an argon atmosphere in the absence of light. After stirring for 1 hour, 2,3-dichloro-4,5-dicyano-1,4-benzoquinone (227 mg, 0.67 mmol) was added and the resulting mixture stirred for an additional 1 hour. Triethylamine (137 [µL, 0.98 mmol) was then added, and the mixture stirred for 5 minutes, and then filtered through a short column of silica using hexanes and dichloroethane to separate out the crude porphyrin. After solvent removal, the title porphyrin was obtained by flash chromatography (6.5 cm diameter, 5.5 cm silica height, eluting with dichloromethane/hexanes, 1:4 to 2:3 gradient) as a purple solid (95 mg, 53%)

EXAMPLE 2

Precursors for Compounds IV and V—2-Formyl-3,8,13,18-tetra-t-butylporphyrin ("TTBP") and 5-formyl-2,7,12,17-tetra-t-butylporphyrin A mixture of dimethylformamide (1.30 mL, 17 mmol) and phosphorus oxychloride (1.30 mL, 14 mmol) was stirred for 10 minutes at 40° C. Ni(II)-2,7,12,17-tetra-t-butylporphyrin ("TTBP") (1.27 g, 2.15 mmol) and dichloroethane (DCE) (70 mL) were then added, and the resulting mixture stirred at 90° C. for 12 hours. The reaction mixture was then poured into a solution of sodium acetate (10.4 g, 77 mmol) in water (5 mL) and heated to reflux for 1 hour. After cooling to RT, DCE and water (150 mL each) were added and the layers separated. The aqueous layer was extracted with DCE (3×150 mL). The combined DCE layers were then washed with $Na_2CO_3$ (1×50 mL) and dried with $MgSO_4$. The filtered solution was concentrated under reduced pressure to ca. 100 mL and preabsorbed onto silica gel (ca. 10 g). The crude products were then isolated by flash column chromatography (silica, DCE/hexanes, 20%–70% gradient). The meso isomer (5-formyl) eluted just after unreacted starting material [Ni(II) TTBP] and was isolated as a purple solid (168 mg, 12.6%). The beta isomer (2-formyl) eluted next, and was isolated as a green solid (532 mg, 40.0%).

The beta (2-formyl) isomer (350 mg) was demetallated by dissolving in the minimum amount of sulfuric acid (80 mL) at RT for 1 minute. The acid solution was then poured into an ice/water mixture (1 Kg/200 mL), neutralized with the minimum amount of NaOH to cause the product to precipitate completely, filtered and washed with warm water. The wet material was then dissolved in a minimum volume of DCE and dried with $MgSO_4$. The solvent was removed under reduced pressure, and the product further dried in vacuo (310 mg, 97%). The same procedure was employed for the demetallation of the meso (5-formyl) isomer.

EXAMPLE 3A

Attachment of TPA Group, 2-[4''-(diphenylamino)-4'-stilbenyl]-1-ethenyl), to meso position of 5-formyl-TTBP to form Compound IV Potassium tert-butoxide (0.2 mL, 1 M solution in THF) was added to a mixture of meso-formyl-TTBP (7.2 mg, 0.013 mmol) and 4'-(diphenylamino)-4-stilbenyl-methyltributylphosphonium bromide (90 mg, 0.14 mmol) in anhydrous THF at 0° C. The mixture was stirred at RT for 20 minutes, then refluxed for 48 hours. After cooling, the product was extracted with methylene chloride, and the resulting solution washed with brine and dried with $MgSO_4$. After the solvent was removed by rotovaporization, the product was purified by basic alumina column chromatography ($CH_2Cl_2$/hexane, 1:1). The product was further purified by recrystallization. from MeOH/$CH_2Cl_2$ (10 mg, 86%).

$^1$H NMR δ: −3.85 (s, 2H, NH), 2.14–2.41 (s, 36 H, CH3),6.97–7.86 (m, 22H, Ar—H and vinyl H), 10.42, 10.45, 10.61 (3 s, meso CH), 9.12, 9.20, 9.22, 10.74 (4s, 4H, pyrrolic-H); $^{13}$C NMR: 34.01, 34.14, 34.52, 34.73, 34.92, 37.05, 37.72, 77.00, 77.43, 77.85, 102.97, 103.10, 105.13, 105.38, 125.78, 127.02, 131.30, 194.55 ppm; MALDI-TOF, m/z: 920.47, 906.36, 848.29, 665.26.

EXAMPLE 3B

Attachment of TPA Group, 2-[4''-(diphenylamino)-4'-stilbenyl]-1-ethenyl), to beta position of 2-formyl TTBP to form Compound V Potassium tert-butoxide (0.15 mL, 1 M solution in THF) was added to a mixture of beta-formyl-TTBP (12.5 mg, 0.022 mmol) and [4'-(diphenylamino)-4-stilbenyl]-methyltributylphosphonium bromide (50 mg, 0.078 mmol) in anhydrous THF at 0° C. The work-up and isolation of the desired product was identical to that described above for the meso isomer (12 mg, 60%).

$^1$H NMR δ: −2.93 (bd. s, 2H, NH), 2.16–2.27 (s, 36 H, CH3), 7.02–7.85 (m, 22H, Ar—H and vinyl H), 9.01, 9,12, 9.22 (3s, 3H, pyrrolic-H), 9.33, 10.20, 10.42 (3s, 4H, meso-H); $^{13}$C NMR: 33.94, 34.15, 35.01, 76.98, 77.40,77.83, 123.51, 123.95.,124.98, 127.01, 127.39, 127.63, 127.87, 129.72 ppm; MALDI-TOF, m/z: 938.60, 906.61, 681.46, 665.47.

EXAMPLE 4

Bis-(4',4''-diphenylamino)stilbene

A 500 mL 3-neck round bottom flask equipped with a reflux condenser, magnetic stir bar, nitrogen inlet and rubber septum was charged with anhydrous THF (150 mL). The flask was cooled to 0° C., and titanium tetrachloride (7.36 mL, 0.0388 mol, 2 eq.) was added dropwise by syringe. Zinc (5.07 g, 0.0776 mol, 4 eq.) was then added in small portions to the emulsion, and the resulting mixture was refluxed for 45 minutes. The reaction mixture was cooled to 0° C. and a solution of 4-formyltriphenylamine (5.3 g, 0.0194 mol, 1 eq.) in anhydrous THF and pyridine (5 mL) was added dropwise from an addition funnel. The mixture was then refluxed, and the progress monitored by TLC (dichloromethane) until completion. The mixture was then cooled and poured into water (80 mL). The resulting emulsion was stirred for 20 minutes and then partitioned in a separatory funnel. The aqueous layer was extracted with dichloromethane (100 mL), and the combined organic layers were washed with water (3×80 mL). The solution was then dried with $MgSO_4$ and the solvent removed by rotovaporization. The resulting solid was recrystallized from ethanol to yield a yellow solid (4.45 g, 90%). $^1$H NMR δ: 6.47–7.45 (m, 30H, Ar—H and CH=CH); $^{13}$C NMR: 122.7, 123.3, 123.6, 124.1, 124.8, 126.9, 127.5, 129.6, 130.2, 132.3, 147.4, 147.9 ppm.

EXAMPLE 5

General Procedure for Oxopropenylation of Diphenylaminophenylaldehydes

A 3-neck round bottom flask equipped with a magnetic stir bar, $CaCl_2$ drying tube, nitrogen inlet and stopper was charged with the selected aldehyde in anhydrous THF (1 eq.). Tributyl(1,3-dioxolan-2-ylmethyl)phosphonium bromide in THF (1.1 eq.) was added, then potassium tert-butoxide (1.4 eq.) was added in small portions. The reaction was stirred at RT until completion as indicated by TLC (1:1 dichloromethane:hexane). After completion, aqueous HCl (2M, 50 mL) was added dropwise, and the resulting bilayer separated. The aqueous layer was extracted with dichloromethane (3×75 mL), and the combined organic solution was washed with water (3×75 mL) and dried with $MgSO_4$. The solvent was removed by rotovaporization and the resulting solid purified by silica gel chromatography (1:1 dichloromethane:hexane).

The following compounds are provided as examples of this general extension procedure:

3-[4'-(diphenylamino)phenyl]-2-propenal (72%), m.p. 109–11° C., λmax 395 nm (amax 35,179); $^1H$ NMR δ: 6.62–6.55 (dd, 1 H, Jab=15.8, Jbc=7.8 Hz, =CHCHO), 6.99–7.41 (m, 15H, Ar—H, and 1 vinyl H), 9.60–9.62 (d, Jbc=7.8 Hz, CHO), $^{13}C$ NMR: 121.4, 124.8, 126.1, 126.4, 127.1, 129.9, 130.2, 146.9, 151.2, 153.0, 194.1 ppm.

5-[4'-(diphenylamino)phenyl]-2,4-pentadienal (73%), m.p. 137–9° C., λmax. 413 nm (amax 43,904), $^1H$ NMR δ: 6.18–6.26 (dd, 1H, Jab=15 Hz, Jbc=8 Hz, =CHCHO), 6.82–7.36 (m, 17H, Ar—H and 1 vinyl H), 9.60 (d, 1 H, Jbc=8 Hz, CHO), $^{13}C$ NMR: 122.3, 124.3, 124.4, 125.2, 125.7, 129.0, 129.8, 130.8, 142.7, 147.3, 149.7, 153.1, 193.9 ppm.

EXAMPLE 6

General Procedure for the Synthesis of α,ω-bis-(diphenylamino)diphenylpolyenes

A 3-neck round bottom flask equipped with a magnetic stir bar, $CaCl_2$ drying tube, nitrogen inlet and stopper was charged with the appropriate aldehyde (1 eq.) in anhydrous THF. A bis-Wittig salt (0.5 eq.) in THF is then added: (E)-but-2-en-1,4-diyl-bis(tributylphosphonium) dichloride for polyenes with an odd number of double bonds, and (E,E)-hexa-2,4-dien-1,6-diyl-bis-(tributylphosphonium) dibromide for polyenes with an even number of double bonds. Potassium tert-butoxide (2.2 eq.) is then added in small portions, and the reaction mixture is stirred at RT until completion as indicated by TLC (dichloromethane). The solvent is removed by rotovaporization, and the impure product is purified by silica gel column chromatography (dichloromethane).

The following compounds are provided as examples of this general synthesis procedure:

Bis-(4',4"-diphenylamino)-1,6-diphenyl-1,3,5-hexatriene (82%); λmax 420 nm (amax, 64,630); $^1H$ NMR δ: 6.4–6.8 (m, 6H, vinyl), 7.00–7.23 (m, 28 H, Ar—H); $^{13}C$ NMR: 123.4, 123.9, 124.9, 127.6, 128.2, 129.7, 132.1, 133.4, 147.5, 147.9 ppm.

Bis-(4',4"-diphenylamino)-1,8-diphenyl-1,3,5,7-octatetraene (81%); λmax 434 nm amax (35,588); $^1H$ NMR δ: 6.30–6–89 (m, 8H, vinyl), 7.02–7.25 (m, 28H, Ar—H); $^{13}C$ NMR: 123.5, 123.9, 124.9, 127.6, 128.1, 129.6, 132.2, 133.2, 133.7, 147.5, 147.9 ppm.

EXAMPLE 7

4-(Diphenylamino)-4'-formylstilbene

Potassium tert-butoxide (0.044 mol, 44mL 1M solution in THF) was added to a mixture of terephthalaldehyde mono-(diethyl acetal) (Sigma-Aldrich) (9.98 g, 0.048 mol) and 4-(diphenylamino)benzyltributylphosphonium bromide (21.6 g, 0.040 mol) in anhydrous THF (200 mL) in a 500 mL round bottom flask equipped with a reflux condenser, addition funnel and nitrogen inlet. After the addition was complete, the mixture was refluxed for 2 hours, and then cooled to RT. Aqueous HCl (20 mL, 3M) was then added and the mixture was stirred an additional hour. The product was extracted with methylene chloride (3×100 mL) and the combined organic solution dried with $MgSO_4$. The solvent was removed by rotovaporization and the crude product purified by silica gel column chromatography (1:1 hexane:methylene chloride) yielding the pure product as a bright yellow solid (13 g, 87%). $^1H$ NMR δ: 7.02–7.85 (m, 18 Ar—H, 2 vinyl H), 9.96 (s, 1H, CHO).

EXAMPLE 8

4-(Diphenylamino)-4'-hydroxymethylstilbene

A 500 mL round bottom flask was charged with LAH (0.228 g, 0.006 mol) in THF (1 M solution), and compound 17 (4.38 g, 0.0117 mol) dissolved in anhydrous THF (100 mL) was added dropwise via an addition funnel. The solution was stirred at RT for 4 hours, cooled to 0° C., and then water was added to quench the unreacted LAH. The reaction was neutralized with aqueous HCl (4 mL, 3M), and stirred an additional 1 hour. The product was extracted with methylene chloride (3×100 mL), and the combined organic product was washed with water (3×100 mL) and dried with $MgSO_4$. After solvent removal by rotovaporization, the product was purified by silica gel column chromatography (4:1 benzene:ethyl acetate) yielding 4-(Diphenylamino)-4'-hydroxymethylstilbene as a yellow solid (3.3 g, 75%). $^1H$ NMR δ: 4.68 (s, 2H, CH2),7.04–7.45 (m, 18 Ar—H, 2 vinyl H).

EXAMPLE 9

[4-(Diphenylamino)-4"-stilbenyl] methyltributylphosphonium bromide 4-(Diphenylamino)-4'-hydroxymethylstilbene (1.0 g, 0.00265 mol) was dissolved in anhydrous THF (10 mL) and added to a mixture of phosphorus tribromide (0.41 g, 0.0015 mol) in anhydrous THF (10 mL) under a nitrogen atmosphere. The resulting mixture was stirred at 0° C. for 2 hours, and then for an additional 16 hours at RT. The product was extracted with methylene chloride, dried with $MgSO_4$ filtered and the solvent removed by rotovaporization. The product was purified by silica gel column chromatography ($CH_2Cl_2$), dissolved in toluene and reacted with tributylphosphine (0.54 g, 0.00265 mol). The resulting solution was refluxed for 72 hours and the product obtained by solvent removal as a glassy solid. The product was dissolved in THF to be used directly in the preparation of IV and V (L 18 g, 69%). $^1H$ NMR δ: 0.91 (t, 9H, CH3), 1.47 (m, 12H, CH2), 2.41 (m, 6H, CH2), 4.23 (m, 2H, CH2), 7.0–7.67 (m, 18 Ar—H, 2 vinyl H).

EXAMPLE 10

Preparation of Precursors for Thienyl-Containing Chromophores

2-Butylthiothiophene (44)

A solution of n-butyllithium (1.6 M in hexane, 0.304 mol, 189.8 mL) was added dropwise to a solution of thiophene (Aldrich) (24.3 g, 0.289 mol) and TMEDA ( 45.8 mL, 0.304 mol) in THF (200 mL) at room temperature. The resulting mixture was refluxed for 0.5 hours, cooled in an ice-bath, and powdered sulfur (9.7 g, 0.304 mol) added carefully. After the resulting mixture had become clear, iodobutane (37.9 mL, 0.333 mol) was added dropwise. The product mixture was then stirred at room temperature overnight, poured into cold water and extracted with ethyl ether (3×150 mL). The combined extracts were washed with saturated brine and dried (MgSO$_4$). After removal of the drying agent by filtration, the solvent was removed using a rotary evaporator. The product was obtained as colorless liquid by vacuum distillation (36.2 g, 73%). b.p. 88–90° C. (1 Torr); $^1$H NMR δ: 0.89 (t, 3 H, J=7.3 Hz CH$_3$), 1.4(m, 2H, CH$_3$—CH$_2$),1.58 (m, 2 H, CH$_3$—CH$_2$—CH$_2$), 2.78 (t, 2 H, J=7 Hz, CH$_2$—S), 6.95 (dd, 1 H J=5.3 Hz, J=3.6 Hz, aromatic H), 7.08 (d, 1 H, J=3.6 Hz, aromatic H), 7.3 (d, 1 H, J=5.3 Hz, aromatic H); λmax/nm ($\epsilon_{max}$/dm$^3$ mol$^{-1}$cm$^{-1}$) 274 (5500); HRMS (EI) calc. for C$_8$H$_{12}$S$_2$: 172.0375, found 172.0380.

5-Butylthiothiophene-2-carbaldehyde (45)

POCl$_3$ (1.7 mL, 0.019 mol) was added dropwise to a solution of 44 (2 g, 0.116 mol) and dry DMF (1.8 mL, 0.023 mol) in 1,2-dichloroethane(75 mL) at 0° C. The resultant mixture was refluxed for 2 hours, poured into ice water and neutralized by addition of 6 M sodium carbonate solution. The reaction mixture was extracted with methylene chloride (3×100 mL). The combined extracts were washed with saturated brine and dried (MgSO$_4$). After removal of the drying agent by filtration, methylene chloride was removed using a rotary evaporator. The residue was purified by column chromatography over silica gel, eluting with CH$_2$Cl$_2$. The product was obtained as orange liquid (2.2 g, 95%); $^1$H NMR δ: 0.94 (t, 3 H, J=7.3 Hz, CH$_3$), 1.46 (m, 2 H, CH$_3$—CH$_2$), 1.7 (m, 2 H, CH$_3$—CH$_2$—CH$_2$), 3.01 (t, 2 H, J=7.3 Hz, CH$_2$—S), 7 (d, 1 H, J=3.8 Hz, aromatic H), 7.61 (d, 1 H, J=3.8 Hz, aromatic H), 9.76 (s, 1 H, CHO); $\lambda_{max}$/nm ($\epsilon_{max}$/dm$^3$ mol$^{-1}$cm$^{-1}$) 42.5 (11,700); HRMS(EI$^+$) calculated for C$_9$H$_{12}$OS$_2$: 200.0320, found 200.0329. The product was used without further purification in the preparation of 46.

2-Hydroxymethyl-5-butylthiothiophene (46)

A solution of NaBH$_4$ (5.3 g, 0.141 mol) in methanol (29.0 g) and sodium hydroxide (20%, 56.0 mL) was added dropwise to a solution of 45 (56.47 g, 0.282 mol) in THF (75 mL) at room temperature. The mixture was stirred for 2 hours, extracted with ethyl ether 3×150 mL), the combined extracts washed with brine and dried (MgSO$_4$). After solvent removal, the crude product 46 was obtained as an oil (55.4 g, 97%); $^1$H NMR δ: 0.88 (t, 3 H, J=7.3 Hz, CH$_3$), 1.39 (m, 2 H, CH$_3$—CH$_2$), 1.57 (m, 2 H, CH$_3$—CH$_2$—CH$_2$),1.88 (s, 1 H OH), 2.76 (t, 2 H, J=7.3 Hz, CH$_2$—S), 4.73 (s, 2 H, CH$_2$—OH), 6.83 (d, 1 H, J=3.5 Hz, aromatic H), 6.94 (d, 1 H, J=3.5 Hz, aromatic H); $\lambda_{max}$/nm ($\epsilon_{max}$/dm$^3$ mol$^{-1}$cm$^{-1}$) 275.5 (3600); LRMS(EI$^+$) calc. for C$_9$H$_{14}$OS$_2$: 202.1, found 202.1. The product was used without further purification in the preparation of 47.

2-Bromomethyl-5-butylthiothiophene (47)

A solution of crude 46 (55.4 g, 0.274 mol) in anhydrous ethyl ether (70 mL) was added dropwise to a solution of phosphorus tribromide (12.9 mL, 0.137 mol) in anhydrous ethyl ether (300 mL) at 0° C. After addition was complete, the mixture was allowed to warm slowly to room temperature and stirred for 4 hours under nitrogen. The mixture was then extracted with ethyl ether (3×150 mL). The combined organic solution was washed with brine and dried (MgSO$_4$). MgSO$_4$ was removed by filtration and the crude product was carried to the next step without the removal of solvent to prevent product decomposition.

(5-Butylthio-2-thienyl)tributyl methyl phosphonium bromide (48)

Tributylphosphine (68.5 mL, 0.274 mol) was added to a solution of crude 47 in ethyl ether at room temperature. The mixture was stirred under nitrogen for 48 hours. The white solid product was obtained by filtration (93 g, 73%) and used without further purification. m.p., 102–104° C.; $^1$H NMR δ: 0.91 (m, 12 H CH$_3$), 1.46 (m, 16 H, CH$_3$—CH2), 2.42 (m, 6 H, P—CH$_2$—CH$_2$), 2.74 (m, 2 H S—CH$_2$), 4.55 (s, 1 CH$_2$—P), 4.6 (s, 1 H, CH$_2$—P), 6.96 (d, 1 H, J=3.5 Hz, aromatic H), 7.22(d, 1 H, J=3.5 Hz, aromatic H); $\lambda_{max}$/nm ($\epsilon_{max}$/dm$^3$ mol$^{-1}$cm$^{-1}$) 283.5 (870) (Anal. Calc. for C$_{21}$H$_{40}$BrPSO$_2$: C, 53.95; H, 8.62. Found: C, 54.03; H, 8.61.)

2-(3'-Iodopropoxy) tetrahydro-2H-pyran (59)

2-(3'-Chloropropoxy) tetrahydro-2H-pyran (Aldrich) (9 g, 0.05 mol) was added to a solution of sodium iodide (37.8 g, 0.25 mol) in acetone (250 mL) with stirring. The resultant slurry was refluxed for 48 hours. The mixture was cooled, evaporated to a solid mass and transferred to the top of a short column of neutral alumina. The column was washed with CH$_2$Cl$_2$ (1 L) and CH$_2$Cl$_2$ was removed using a rotary evaporator. The product was obtained as yellow liquid (12.6 g, 93%). $^1$H NMR δ: 1.62–1.86 (m, 6 H, ring CH$_2$), 2.07 (m, 2 H, CH$_2$—CH$_2$—I), 3.27 (m, 2 H, CH$_2$—I), 3.38–3.54 (m, 2 H, CH$_2$—O), 3.74–3.89 (m, 2 H ring O—CH$_2$), 4.58 (t, 1 H, J=3.2 Hz, ring CH); $\lambda_{max}$/nm ($\epsilon_{max}$/dm$^3$ mol$^{-1}$ cm$^{-1}$) 267 (1500); HRMS (EI$^+$) calc. for C$_8$H$_{15}$IO$_2$: 269.0049. found 269.0039.

2-(3'-Hydroxypropylthio)thiophene

A solution of n-butyllithium 1.6 M in hexane, 0.045 mol, 28.2 mL) was added dropwise to a solution of thiophene (3.62 g, 0.043 mol) and TMEDA (5.22 g, 0.045 mol) in THF (200 mL) at room temperature. The resulting mixture was refluxed for 0.5 hours, cooled in an ice-bath and powdered sulfur (1.44 g, 0.045 mol) added carefully with stirring. After the resulting mixture had become clear, 59 (12.55 g, 0.049 mol) was added dropwise. The product mixture was then stirred at room temperature overnight, poured into cold water and extracted with ethyl ether (3×150 mL). The combined extracts were washed with brine, dried (MgSO$_4$) and solvent was evaporated. The product was obtained as colorless liquid by vacuum distillation (4.8 g, 64% ). b.p. 138–140° C. (1 Torr); $^1$H NMR δ: 1.58 (s, 1 H, OH), 1.86 (m, 2 H, CH$_2$—CH$_2$—OH), 2.9 (t, 2 H, J=7.1 Hz, S—CH$_2$), 3.76 (t, 2 H, J=6.1 Hz, CH$_2$—OH), 6.97 (dd, 1 H, J=5.3 Hz, J=3.2 Hz, aromatic H), 7.12 (d, 1 H, J=3.2 Hz, aromatic H), 7.34 (d, 1 H, J=5.3 Hz, aromatic H); $\lambda_{max}$/nm ($\epsilon_{max}$/dm$^3$ mol$^{-1}$cm$^{-1}$) 272.5 (3900); HRMS (EI$^+$) calc. for C$_7$H$_{10}$OS$_2$: 174.0173. found 174.0173.

2-(3'-Acetoxypropylthio)thiophene (61)

Acetic anhydride (42.9 mL, 0.455 mol) was added to a solution of 60 (13 g, 0.075 mol) in pyridine (57.3 mL, 0.71 mol ) at room temperature. The mixture was stirred overnight, and then water (100 mL) was added dropwise with an ice-bath cooling. The resultant mixture was stirred for 2 hours and extracted with ethyl ether (3×100 mL). The organic layer was washed with water (3×200 mL) to remove pyridine. The combined extracts were washed with brine, dried (MgSO$_4$) and solvent was evaporated. The product was obtained as yellow liquid (14.5 g, 84%). $^1$H NMR δ: 1.92 (m, 2 H, CH$_2$—CH$_2$—OCOCH$_3$), 2.03 (s, 3 H, CH$_3$), 2.84 (t, 2 H, J=7.2 Hz, S—CH$_2$), 4.16 (t, 2 H, J=6.3 Hz, CH$_2$—OCOCH$_3$), 6.98 (dd, 1 H, J=5.2 Hz, J=3.5 Hz, aromatic H), 7.13 (d, 1 H, J=3.5 Hz, aromatic H), 7.35 (d, 1 H, J=5.2 Hz, aromatic H); λ$_{max}$/nm (ε$_{max}$/dm$^3$ mol$^{-1}$cm$^{-1}$) 272 (3700). HRMS (EI$^+$) calc. for C$_9$H$_{12}$O$_2$S$_2$: 216.0275. found 216.0279. The product was used directly without further purification in the preparation of 62.

5-(3'-Acetoxypropylthio)thiophene-2-carbaldehyde (62)

POCl$_3$ (3.4 mL, 0.036 mol) was added dropwise to a solution of 61 (4.9 g, 0.023 mol) and dry DMF (3.5 mL, 0.045 mol) in 1,2-dichloroethane (100 mL) at 0° C. The resultant mixture was refluxed for 2 hours, poured into ice water and neutralized by addition of 6 M sodium carbonate. The reaction mixture was extracted with methylene chloride (3×100 mL). The combined extracts were washed with saturated brine, dried (MgSO$_4$). After filtration, methylene chloride was removed using a rotary evaporator. The residue was purified by column chromatography over silica gel, eluting with 10% ethyl acetate in methylene chloride. The product was obtained as orange liquid (4.5 g, 82%). $^1$H NMR δ: 2 (m, 2 H, CH$_2$—CH$_2$—OCOCH$_3$), 2.03 (s, 3 H, CH$_3$), 3.04 (t, 2 H, J=7.2 Hz, S—CH$_2$), 4.15 (t, 2 H, J=6.2 Hz, CH$_2$—OCOCH$_3$), 7.04 (d, 1 H, J=3.9 Hz, aromatic H), 7.59 (d, 1 H, J=3.9 Hz, aromatic H), 9.75 (s, 1 H, CHO); λ$_{max}$/nm (ε$_{max}$/dm$^3$ mol$^{-1}$cm$^{-1}$) 339 (14,200); HRMS (EI$^+$) calc. for C$_{10}$H$_{12}$O$_3$S$_2$: 244.0231. found 244.0228. The product was used without further purification in preparation of 63.

3-(5'-Hydroxypropylthio-2'-thienyl)-2-propenal (63)

A solution of potassium tert-butoxide (1 M in hexanes, 0.047 mol, 47 mL) was added dropwise to a solution of 62 (7.63 g, 0.031 mol) and (1,3-dioxalane-2-ylmethyl) tributylphosphonium bromide (1 M in THF, 0.038 mol, 37.5 mL) in dry THF (150 mL) at room temperature. The resulting mixture was stirred overnight, and then poured into water. The product and tributylphosphine oxide were extracted with ethyl ether (3×150 mL), and the combined extracts were washed with saturated brine, and dried (MgSO$_4$). After filtration, ether was removed by rotary evaporator and the residue dissolved in THF (100 mL). Aqueous HCl (3 M, 120 mL) was then added dropwise, and the resulting mixture stirred at room temperature for 2 hours, after which it was poured into water, extracted and washed as described above and dried. After filtration and removal of solvent, the residue was purified by column chromatography over silica gel, eluting with 50% ethyl acetate in methylene chloride. The product was obtained as red liquid (4.5 g, 63%). $^1$H NMR δ: 1.55 (s, 1 H, OH), 1.9 (m, 2 H, CH$_2$—CH$_2$—OH), 3.03 (t, 2 H, J=7.1 Hz, S—CH$_2$), 3.76 (t, 2 H, J=6 Hz, CH$_2$—OH), 6.37 (dd, 1 H, J=15.6 Hz, J=7.7 Hz, =CHCHO), 7.01 (d, 1 H, J=3.8 Hz, aromatic H), 7.18 (d, 1 H, J=3.8 Hz, aromatic H), 7.44 (d, 1 H, J=15.6 Hz, vinyl), 9.57 (d, 1 H, J=7.7 Hz, CHO); λ$_{max}$/nm (ε$_{max}$/dm$^3$ mol$^{-1}$cm$^{-1}$) 354.5 (17,400) HRMS (EI) Calc. for C$_{10}$H$_{12}$O$_2$S$_2$: 288.0281. found 288.0279. The product was used without further purification in the preparation of 65.

EXAMPLE 11

Preparation of Thienyl-Containing Chromophores

1-[5'-Butylthio-2'-thienyl]-2-[5"-(3'"-hydroxypropylthio)-2"-thienyl] ethene (64)

A solution of sodium ethoxide (1 M in ethanol, 0.062 mol, 62 mL) was added dropwise to a solution of 62 (6 g, 0.025 mol) and 48 (13.78 g, 0.03 mol) in ethanol (75 mL) at room temperature. The resulting mixture was stirred at 60° C. overnight, after which it was cooled to room temperature. After removal of ethanol, the residue was purified by column chromatography over silica gel, eluting with methylene chloride. The product was obtained as yellow solid (8.7 g, 96%). m.p. 56–57° C.; $^1$H NMR δ: 0.89 (t, 3 J=7.3 Hz, CH3), 1.36 (s, 1 H, OH), 1.39 (m, 2 H, CH2-CH3), 1.59 (m, 2 H, CH2-CH2CH3),1.88 (m, 2 H, CH2-CH2-OH), 2.8 (t, 2 H, J=7.3 Hz, S—CH2), 2.92 (t, 2 H, J=7.1 Hz, S—CH2-CH2-CH2-OH), 3.76 (t, 2 H, J=5.9 Hz, CH2-OH), 6.46–6.97 (m, 6 H, vinyl and aromatic H); $^{13}$C NMR: 14.05, 22.03, 31.92, 32.44, 35.6, 38.81, 61.55, 121.67, 122.05, 122:73, 123.37, 126.97, 127.09, 133.74, 134.31, 145.01, 145.34; λ$_{max}$/nm (ε$_{max}$/dm$^3$ mol$^{-1}$cm$^{-1}$) 368 (18,700); (Anal. Calc. for C$_{17}$H$_{22}$OS$_4$: C, 55.09; 11, 5.99. Found: C, 55.09; H, 6.02)

1-[5'-Butylthio-2'-thienyl]-4-[5"-(3'"-hydroxypropylthio)-2"-thienyl]-1,3-butadiene (65)

A solution of sodium ethoxide (1 M in ethanol, 0.024 mol, 24 mL) was added dropwise to a solution of 63 (2.7 g, 0.012 mol) and 48 (6.73 g, 0.014 mol) in ethanol (75 mL) at room temperature. The resulting mixture was stirred at 60° C. overnight after which it was cooled to room temperature. After removal of ethanol, the residue was purified by column chromatography over silica gel, eluting with methylene chloride. The product was obtained as yellow solid (4 g, 85%). m.p. 72.5–74.5° C.; $^1$H NMR δ: 0.89 (t, 3H, J=7.3 Hz, CH3), 1.41 (m, 2 H, CH3—CH2), 1.6 (m, 2 H, CH3-CH2-CH2), 1.87 (m, 2 H, CH2-CH2-OH), 2.8 (t, 2 H, J=7.3 Hz, CH2-S), 2.91 (t, 2 H, J=7.1 Hz, S—CH2), 3.76 (t, 2 H, J=6.1 Hz, CH2-OH), 6.57–6.96 (m, 8 H, aromatic and vinyl H); $^{13}$C NMR: 14.05, 22.03, 31.92, 32.44, 35.60, 38.81, 61.55, 125.77, 126.08, 126.82, 126.90, 128.90, 129.23, 133.78, 134.21, 134.34, 135.22, 146.00, 146.50 ppm; λ$_{max}$/nm (ε$_{max}$/dm$^3$ mol$^{-1}$cm$^{-1}$) 390 (45,000); (Anal. Calc. for C$_{19}$H$_{24}$OS$_4$: C, 57.53; H, 6.10. Found: C, 57.41; H, 6.12.)

1-[5'-Butylthio-2'-thienyl]-2-[5'-(3'"-iodopropylthio)-2"-thienyl] ethene (66)

Iodine (6.17 g, 0.025 mol) was added slowly to a solution of triphenylphosphine (6.38 g, 0.025 mol) and imidazole (1.65 g, 0.025 mol) in a 1:3 mixture of acetonitrile: ether (100 mL) at 0° C. The ice bath was removed and the mixture was stirred for 15 minutes. Compound 64 (3 g, 0.008 mol) in 1:3 acetonitrile: ether mixture (20 mL) was added dropwise. The resulting mixture was stirred for an hour at room temperature. After removal of the solvent the residue was purified by column chromatography over silica gel, eluting with 5% ethyl acetate in hexanes to yield 66 (3.7 g, 95.8%). The product was obtained as gel, therefore melting point could not be determined. $^1$H NMR δ: 0.89 (t, 3 H, J=7.3 Hz, CH3), 1.41 (m, 2 H, CH2-CH2), 1.6 (m, 2 H, CH2-CH2-CH3), 2.08 (m, 2 H, CH2-CH2-I), 2.81 (t, 2 H, J=7.3 Hz, S—CH2), 2.88 (t, 2 H, J=6.9 Hz, S—CH2), 3.28 (t, 2 H, J=6.7 Hz, CH$_2$—I), 6.84–6.97 (m, 6 H, aromatic and vinyl H); λ$_{max}$/nm (ε$_{max}$/dm$^3$ mol$^{-1}$cm$^{-1}$) 373 (45,500); (Anal. Calc. for C$_{17}$H$_{21}$IS$_4$: C, 42.45; H, 4.51. Found: C, 42.70; H, 4.34.) The product was used without further purification in the preparation of 69.

1-[5'-Butylthio-2'-thienyl]-4-[5"-(3'"-iodopropylthio)-2"-thienyl]-1,3-butadiene (67)

Compound 67 was prepared from 65 (2 g, 0.005 mol), iodine (3.85 g, 0.015 mol), triphenyl phosphine (3.94 g, 0.015 mol) and imidazole (1.02 g, 0.015 mol) as described above for the preparation of 66. The crude product was purified by column chromatography over silica gel, eluting with 5% ethyl acetate in hexanes to yield 67 (2.4 g, 95%). The product was obtained as gel, therefore the melting point could not be determined. $^1$H NMR δ: 0.89 (t, 3 H, J=7.3 Hz, CH3),1.4 (m, 2 H, CH2-CH3),1.59 (m, 2 H, CH2-CH2-CH3), 2.09 (m, 2 H, CH2-CH2-I), 2.8 (t, 2 H, J=7.3 Hz, S—CH2), 2.87 (t, 2 H, J=6.9 Hz, S—CH2), 3.28 (t, 2 H, J=6.7 Hz, CH$_2$I), 6.54–6.96 (m, 8 H, aromatic and vinyl H); $\lambda_{max}$/nm ($\epsilon_{max}$/dm$^3$ mol$^{-1}$cm$^{-1}$) 390 (66,600); (Anal. Calc. for C$_{19}$H$_{23}$IS$_4$: C, 45.05; H, 4.58. Found: C, 45.70; H, 4.58.). The product was used without further purification in the preparation of 69.

3,5-Bis-[2'-(5"-butylthio-2"-thienyl)-1'-(5"'-thiopropyleneoxy-2"'-thienyl)ethene] benzyl alcohol (68)

A mixture of 66 (3.72 g, 7.74 mmol), 3,5-dihydroxybenzyl alcohol (Aldrich) (0.53 g, 3.78 mmol), potassium carbonate (1.05 g, 7.56 mmol) and 18-Crown-6 (Aldrich) (0.2 g, 0.78 mmol) in dry 1,4-dioxane (75 mL) was refluxed under a nitrogen atmosphere for 48 hours. The mixture was cooled and evaporated to dryness. The residue was proportioned between methylene chloride (50 ml,) and water (50 mL). The aqueous layer was extracted with methylene chloride (3×75 mL). The combined organic layers were dried over MgSO$_4$. After filtration and removal of solvent, the residue was purified by column chromatography over silica gel, eluting with methylene chloride to yield 68 (2.07 g, 65%). The product was obtained as gel, therefore melting point could not be determined. $^1$H NMR δ: 0.89 (t, 6 H, J=7.3 Hz, CH3), 1.41 (m, 4 H, CH2-CH3), 1.55 (s, 1 H, OH), 1.6 (m, 4 H, CH2-CH2-CH3), 2.06 (m, 4 H, CH2-CH2-O), 2.8 (t, 4 H, J=7.3 Hz, S—CH2), 2.97 (t, 4 H, J=7 Hz, S—CH2), 4.03 (t, 4 H, J=5.9 Hz, CH2O), 4.59 (d, 2 H, J=5.7 Hz, CH2-OH), 6.33 (s, 1 H, phenyl H), 6.48 (s, 2 H, phenyl H), 6.82–6.96 (m, 12 H, aromatic and vinyl H); $^{13}$C NMR: 14.05, 22.03, 29.47, 31.92, 35.57, 38.80, 65.71, 66.21, 101.04, 105.67, 121.66, 122.07, 122.72, 123.25, 126.97, 127.12, 133,73, 134.42, 143.79, 145.32, 145.97, 160.57 ppm; $\lambda_{max}$/nm ($\epsilon_{max}$/dm$^3$ mol$^{-1}$cm$^{-1}$) 373 (54,700); (Anal. Calc. for C$_{41}$H$_{48}$O$_3$S$_8$: C, 58.25; H, 5.72. Found: C, 58.39; H, 5.71.)

3,5-Bis-[4'-(5"-butylthio-2"-thienyl)-1'-(5"'-thiopropyleneoxy-2"'-thienyl)-1,3-butadiene] benzyl alcohol (69)

A mixture of 67 (1.9 g, 3.75 mmol), 3,5-dihydroxybenzyl alcohol (0.25 g, 1.79 mmol), potassium carbonate (0.5 g, 3.58 mmol) and 18-Crown-6 (0.1 g, 0.36 mmol) in dry 1,4-dioxane (75 mL) was refluxed under a nitrogen atmosphere for 48 hours. The mixture was cooled and evaporated to dryness. The residue was proportioned between methylene chloride (50 mL) and water (50 mL). The aqueous layer was extracted with methylene chloride (3×75 mL). The combined organic layers were dried (MgSO$_4$) and after filtration and removal of solvent, the residue was purified by column chromatography over silica gel, eluting with ethylene chloride to yield 69 (1.15 g, 76%). The product was obtained as gel, therefore, melting point could not be determined. $^1$H NMR δ: 0.92 (t, J=7.2 Hz, CH3), 1.43 (m, 4 H, CH2-CH3), 1.61 (m, 4 H, CH2-CH2CH3), 2.09 (m, 4 H, CH2-CH2-O), 2.82 (t, 4 H, J=7.3 Hz, S—CH2), 2.99 (t, 4 H, J=7 Hz, S—CH2), 4.06 (t, 4 H, J=5.8 Hz, CH2-O), 4.62 (s, 2 H, CH2-O), 6.36 (s, 1 H, phenyl H), 6.5 (s, 2 H, phenyl H), 6.55–6.98 (m, 16 H, aromatic and vinyl H); $\lambda_{max}$/nm ($\epsilon_{max}$/dm$^3$ mol$^{-1}$cm$^{-1}$) 390 (86,800); $^{13}$C NMR: 14.02, 22.02, 29.45, 31.92, 35.56, 38.80, 65.76, 66.22, 101.05, 105.68, 125.74, 126.11, 126.80, 126.91, 128.87, 129.25, 133.78, 134.11, 134.45, 135.23, 143.75, 145.98, 146.59, 160.59 ppm; (Anal. Calc. for C$_{45}$H$_{52}$O$_3$S$_8$: C, 60.23; H, 5.84. Found: C, 60.28; H, 5.88.)

EXAMPLE 12

Preparation of Triphenylamine Derivatives 4-(N,N-diphenylamino)benzyl acetate 4-(N,N-Diphenylamino)benzyl alcohol (5.94 g, 0.0216 mol), pyridine (16 mL) and acetic anhydride (11.4 mL) were mixed in a three-neck flask equipped with a condenser and addition funnel. The resulting mixture was stirred overnight at room temperature. Deionized water (50 mL) was then added and the resulting mixture stirred for 2 hours. The product was obtained by filtration, and recrystallized from hexane to yield the desired product (6.52 g, 95%). m.p. 105–6° C.; $^1$H NMR δ: 2.10 (s, 3H, CH3), 5.04 (s, 2H, CH2), 7.0–7.4 (m, 14H, phenyl). Analysis: Calculated for C$_{19}$H$_{17}$NO$_2$: C, 79.46%; H, 6.03%; N, 4.41%. Found: C, 79.37 %; H, 5.72 %; N, 4.41%.

4-[4'-Formyl-N.N-diphenylamino]benzyl acetate

DMF (2.63 g, 0.036 mol) was added to a three-neck flask (50 mL) equipped with a condenser, CaCl$_2$ drying tube, and a glass stopper and cooled in an ice bath. Phosphorus oxychloride (1.8 g, 0.012 mol) was then added dropwise, and the resulting mixture stirred for 5 minutes and then allowed to warm slowly to room temperature. A solution of 4-(N,N-diphenylamino)benzyl acetate (1.88 g, 0.0059 mol) in DMF (20 mL) was then added dropwise. After addition was complete, the mixture was heated to 70° C. and stirred overnight. The mixture was then poured over ice (20 g) and the product obtained by filtration after slowly neutralizing the solution in an ice bath with saturated sodium acetate solution to pH 6. After washing with deionized water and drying, the product was recrystallized by dissolving in a small quantity of chloroform and pouring into excess hexane to yield the desired product (1.21 g, 60%). m.p. 86–89° C.; $^1$H NMR δ: 2.12(s, 2H, CH3), 5.09 (s, CH2), 7.0–7.37 (m, 12H, phenyl), 7.65–7.70 (d, 2H, phenyl), 9.81 (s, 1H, CHO). Analysis: Calculated for C$_{22}$H$_{19}$NO$_3$: C, 76.52%; H, 5.51%; N, 4.06%. Found: C, 76.27%; H, 5.72%; N, 4.01%.

3-[4'-(4"-Acetoxymethyl-N,N-diphenylamino)phenyl]-2-propenal

A solution of NaOEt in ethyl alcohol (1M, 0.03 mol, 30 mL) was added dropwise to a solution of 4-[4'-Formyl-N.N-diphenylamino]benzyl acetate (3.45 g, 0.01 mol) and tributyl(1,3-dioxolan-2-ylmethyl)phosphonium bromide (0.54 M in DMF, 0.03 mol, 30 mL) in DMF (20 mL). The temperature of the mixture was raised to 90° C. and stirred overnight. After cooling the solution to room temperature, aqueous HCl (3M, 30 mL) was added dropwise, the mixture stirred for 1 hour, poured into ice (75 g), and the product extracted with ethyl ether (3×30 mL). The combined extracts were washed with saturated Na$_2$CO$_3$ solution and brine, dried over MgSO$_4$ and the solvent evaporated. The product was purified by dissolving in warm ethanol, filtering, and evaporating the solvent to yield the desired product (2.80 g, 81%). m.p. 112–115° C.; $^1$H NMR δ: 2.0 (s, 3H, CH3), 4.68 (s, 2H, CH2O),6.53–6.64 (dd, 2H, vinyl), 7.0–7.4 (m, 13H, phenyl), 9.62–9.65 (d, 1H, CHO). Analysis: Calculated for $C_{24}H_{21}NO_3$: C, 77.49%; H, 5.82%; N, 3.76%. Found: C, 77.38%; H, 5.54%; N, 3.62%.

4-[(4',4"-Dibromo)diphenylamino]benzaldehyde

Triphenylamine-4-carbaldehyde (22.0 g, 0.08 mol) was dissolved in chloroform (100 mL) in a 1L Erlenmeyer flask. Glacial acetic acid (250 mL) was then added and the resulting bilayer was stirred while bromine (8.66 mL, 0.169 mol, 2.1 equiv.) was added dropwise via syringe while maintaining the reaction temperature at 25° C. After the addition was complete, the reaction mixture was stirred for 1 hour, after which water (250 mL) was added to the reaction mixture. The organic and aqueous layers were separated, and the aqueous layer was extracted with dichloromethane (2×75 mL). The combined organic product solution was then washed with an aqueous solution of KOH (1 M, 100 mL), followed by water (4×100 mL) and brine (100 mL), and was then dried with $MgSO_4$. The solvent was removed by rotovaporization and the resulting green solid was recrystallized from acetonitrile to afford yellow crystals (33.4 g, 96%). $^1$H NMR δ: 7.75–7.22 (m, 12 H, Ar—H), 9.81 (s, 1H, CHO).

4-(Diphenylamino)benzyl alcohol

Triphenylamine-4-carbaldehyde (93 g, 0.34 mole) dissolved in anhydrous THF (1 equiv.) was added dropwise to a suspension of $LiAlH_4$ (0.34 mol) in anhydrous THF contained in a 2L 3-neck flask equipped with an addition funnel, magnetic stir bar, reflux condenser and stopper maintained at 0° C. After the addition was complete, the reaction mixture was allowed to warm to 25° C., and was stirred for 2 hours. The reaction progress was monitored by TLC. After the reaction was complete, the mixture was again cooled to 0° C., and water (200 mL) was added dropwise via the addition funnel to consume any residual LAH. An aqueous solution of HCl (2M, 200 mL) was then added, and the resulting emulsion was stirred for 10 minutes, and then extracted with dichloromethane (3×150 mL). The combined organic product was then washed with water (100 mL) followed by brine (100 mL) and dried with $MgSO_4$. The solvent was removed by rotovaporization to yield the crude product. The product was recrystallized from hexane to yield, the desired product. m.p. 104–5° C.; $^1$H NMR δ: 4.64 (s, 2H, CH2OH), 7.01–7.27 (m, 14 H, Ar—H); $^{13}$C NMR: 123.2, 124.4, 124.6, 125.0, 128.7, 129.6, 135.4, 148.1 ppm.

Diethyl (4-diphenylamino)benzyl phosphonate

A 1L round bottom flask equipped with a magnetic stir bar was charged with a solution of triphenylphosphine (7.2 g, 0.0275 mol, 1.1 eq) in ethyl ether. Bromine (1.4 mL, 0.0275 mol, 1 eq) was then added via syringe to the stirred solution. A saturated solution of 4-(diphenylamino)benzyl alcohol (6.96 g, 0.025 mol, 1 eq) in ethyl ether was poured into the reaction mixture and stirred for 1.5 hour. A white precipitate formed and was isolated by vacuum filtration. The filtered organic layer was then rotovaporized to yield a red-brown gum, which was then dissolved in toluene (250 mL). Triethylphosphite (4.28 mL, 0.025 mol, 1 eq) was added to the toluene solution, and the resulting mixture was placed in a 500 mL round bottom flask equipped with a reflux condenser, and heated at 120° C. for 16 hours. The reaction was monitored by TLC (4:1 dichloromethane:ethyl acetate). After completion of the reaction, the solvent was removed by rotovaporization and the light yellow liquid product was further purified by column chromatography (4:1 dichloromethane:ethyl acetate) to afford the desired product as a white solid (9.2 g, 93%). $^1$H NMR δ: 1.24–1.34 (t, 6H, J=14 Hz, CH3CH2OP), 3.04–3.11 (dq, 4H, Jab=15 Hz, Jbc=14.6 Hz, CH3CH2OP), 3.97–4.11 (d, 2H, J=21 Hz, ArCH2OP), 6.95–7.21(m, 14H, Ar—H).

4-[(4',4—Dibromo)diphenylamino]benzyl alcohol

Reduction of 4-[(4',4"-dibromo)diphenylamino] benzaldehyde (0.0435 mol) with LAH (0.0435 mol) was carried out as described above for 4-(diphenylamino)benzyl alcohol, to give crude 4-[(4',4"-dibromo)diphenylamino] benzyl alcohol which was purified by silica gel column chromatography eluting with dichloromethane/ethyl acetate (4:1) to give pure 4-[(4',4"-dibromo)diphenylamino]benzyl alcohol (34.4 g, 91%). $^1$H NMR δ: 4.62 (s, 2H, CH2OH), 6.77–7.40 (m, 12H, Ar—H).

4-(4'hydroxymethyl)diphenylaminobenzaldehyde and 4-(hydroxymethyl)-4',4"-diformyltriphenylamine A 3-neck round bottom flask equipped with a nitrogen inlet, drying tube, magnetic stir bar and addition funnel was charged with a solution of 4-[(4',4"-Dibromo) diphenylamino]benzaldehyde (25.08 g, 0.0577 mol, 1 eq.) in anhydrous THF (600 mL). The solution was cooled to −100° C. n-Butyllithium in hexane (2.5 M, 115 mL, 0.289 mol, 5 eq) was transferred to the addition funnel via cannula, and then added dropwise. The temperature was then allowed to rise slowly to −80° C., and DMF (27 mL, 0.346 mol, 6 eq.) in a clean addition funnel was then added dropwise to the reaction mixture. The cooling bath was then removed and the reaction mixture was allowed to warm slowly to room temperature. The progress of the reaction was monitored by TLC (9:1 dichloromethane:ethyl acetate). After completion, an aqueous solution of HCl (2M, 100 mL) was added to the solution, and the aqueous layer was separated from the organic layer, and further extracted with ethyl ether (100 mL). The combined organic product was washed with water (3×100 mL) and once with brine, and then dried with $MgSO_4$. After removal of the solvent by rotovaporization, the crude mixture was purified by silica gel column chromatography (9:1 dichloromethane:ethyl acetate) yielding two pure products, 4-(4'hydroxymethyl) diphenylaminobenzaldehyde (6.17 g, 35%) and 4-(hydroxymethyl)-4',4"diformyltriphenylamine (7.34 g, 37%). 4-(4'hydroxymethyl)diphenylaminobenzaldehyde: $^1$H NMR δ: 4.65 (s, 2H, CH2OH), 6.87–7.79 (m, 13H, Ar—H), 9.87 (s, 1H, CHO). 4-(hydroxymethyl)-4', 4"diformyltriphenylamine: $^1$H NMR δ: 4.66 (s, 2H, CH2OH), 7.1–7.81 (m, 12H, Ar—H), 9.87 (s, 2H, CHO).

Although the foregoing description is directed to the preferred embodiments of the invention, it is noted that other variations and modifications will be apparent to those skilled in the art, and may be made without departing from the spirit or scope of the invention. The complete disclosures of all references cited above are hereby incorporated by reference in their entireties for all purposes.

We claim:

1. A compound comprising the following porphyrin structure:

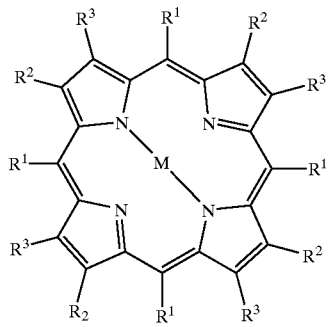

or any pharmaceutically acceptable salt thereof, wherein:

$R^1$ is independently -TPA, -L-TPA, —H, —Ar, —$(CH_2)_n$ $CH_3$, —$CH=CH_2$, —$(CH_2O)_n$-G, -t-Butyl, or —$C(O)$ OG;

$R^2$ is independently -TPA, -L-TPA, —H, —Ar, —$(CH_2)_n$ $CH_3$, —$CH=CH_2$, —$(CH_2O)_n$-G, -t-Butyl, or —$C(O)$ OG;

$R^3$ is independently -TPA, -L-TPA, —H, —Ar, —$(CH_2)_n$ $CH_3$, —$CH=CH_2$, —$(CH_2O)_n$-G, -t-Butyl, or —$C(O)$ OG;

or independently $R^2$ and $R^3$ are linked by —$C_4H_4$— to form a six-member ring;

M is either two hydrogen atoms or a metal ion;

each n is independently an integer ranging from 1 to 20;

each G is independently —H, or a $C_1$ to $C_{20}$ alkyl;

TPA is independently selected from the group consisting of the following structures TPA A through TPA H:

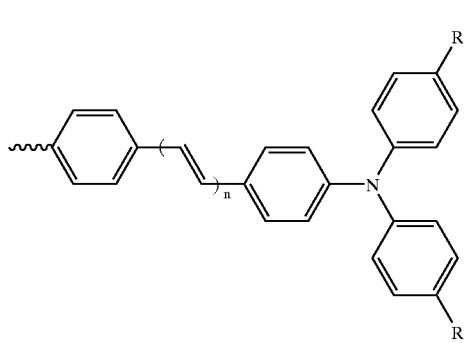
TPA A wherein in TPA A,

R is independently selected from the group consisting of H, alkyl, alkyloxy, and —$(OCH_2CH_2)_mOG$, G is H or alkyl, and m and n independently=1 to 5;

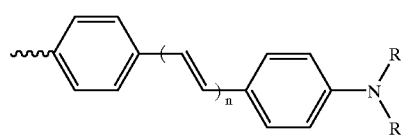
TPA B wherein in TPA B,

R is alkyl, and n=1 to 5;

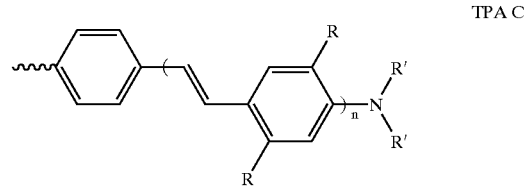
TPA C wherein in TPA C,

R is independently selected from the group consisting of H, CN, alkyl, and alkyloxy, R' is independently selected from the group consisting of alkyl, alkyloxyphenyl, phenyl, and phenyl-$(OCH_2CH_2)_m$ OG, G is H or alkyl, and m and n independently=1 to 3;

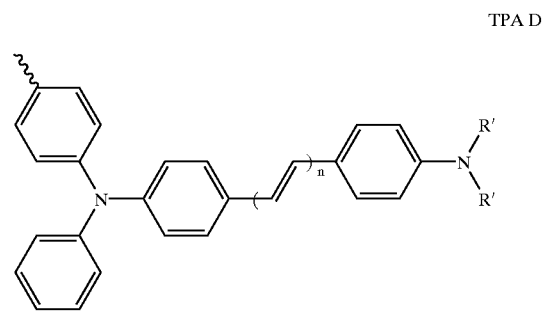
TPA D wherein in TPA D,

R' is independently selected from the group consisting of alkyl, alkyloxyphenyl, and phenyl-$(OGH_2CH_2)_mOG$, G is H or alkyl, and m and n independently=1 to 5;

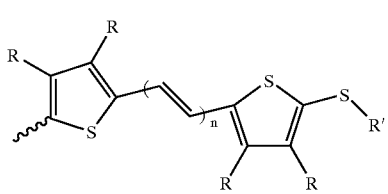
TPA E wherein in TPA E,

R is independently selected from the group consisting of H, alkyl, and —$OCH_2CH_2)_mOG$, R' is alkyl, G is H or alkyl, and m and n independently=1 to 5;

TPA F

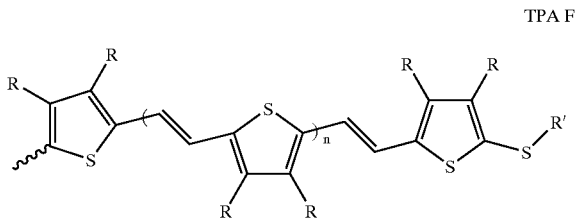

wherein in TPA F,
R is independently selected from the group consisting of H, alkyl, and —(OCH$_2$CH$_2$)$_m$OG,
R' is alkyl,
G is H or alkyl, and
m and n independently=1 to 3;

TPA G

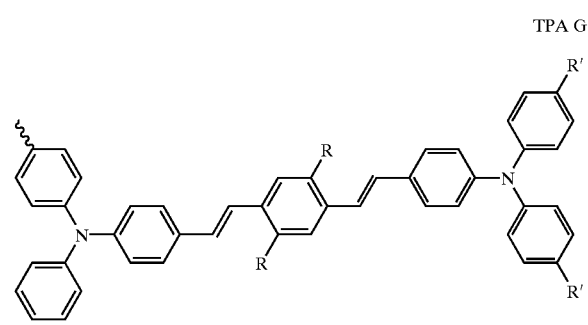

wherein in TPA G,
R is independently selected from the group consisting of H, CN, alkyl, alkyloxy, and —(OCH$_2$CH$_2$)$_m$OG,
R' is independently selected from the group consisting of H, alkyl, alkyloxy, and —(OCH$_2$CH$_2$)$_m$OG,
G is H or alkyl, and
m=1 to 6; and

TPA H

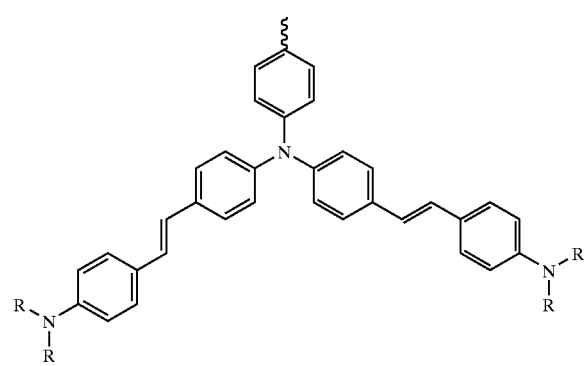

wherein in TPA H,
R is independently selected from the group consisting of alkyl, phenyl, alkyloxyphenyl, and phenyl-[(OCH$_2$CH$_2$)$_m$OG]$_x$,
G is H or alkyl,
m=1 to 4; and
x=1 to 4;
wherein in TPA A through TPA H, alkyl is C$_1$ to C$_{20}$ and the selected TPA is attached to the porphyrin structure at the point indicated by the wiggle line;

Ar is independently C$_6$H$_4$X, C$_6$H$_3$X$_2$, C$_6$H$_2$X$_3$, C$_6$HX$_4$, or C$_6$X$_5$, wherein X is independently F, Cl, Br, or I; and
L is a linking moiety between the porphyrin structure and the TPA and is independently selected from the group consisting of ethenyl, ethynyl, —(CH$_2$)$_n$— where n is equal to 1 to 20, ortho-phenyl, meta-phenyl, para-phenyl, —C(=O)—O—, and 4-phenyl-2'-ethynyl;
wherein at least one of R$^1$, R$^2$ or R$^3$ is a -TPA or -L-TPA moiety, and at least one of R$^1$, R$^2$ or R$^3$ is not —H or a -TPA or -L-TPA moiety.

2. A compound according to claim 1, wherein the compound is 5-[4'''-(diphenylamino)-4''-stilbenyl]-15-[2',6'-dichlorophenyl]-21H, 23H-porphyrin.

3. A compound according to claim 1, wherein M is a metal atom.

4. A compound according to claim 1, wherein M is two hydrogen atoms.

5. A photodynamic therapy agent comprising a compound according to any one of claims 1 or 2–4.

6. A method of increasing the multi-photon absorption cross-section of a porphyrin-containing photosensitizer to at least about 30 GM units at about its maximum wavelength for two-photon absorption, comprising:

attaching at least one TPA-chromophore either directly or through a linking moiety to the meso or beta positions of a porphyrin of the porphyrin-containing photosensitizer, and attaching at least one intersystem crossing enhancing substituent to the meso or beta positions of the porphyrin of the porphyrin-containing photosensitizer, wherein the linking moiety is independently selected from the group consisting of ethenyl, ethynyl, —(CH$_2$)$_n$— where n is equal to 1 to 20, ortho-phenyl, meta-phenyl, para-phenyl, —C(=O)—O— and 4-phenyl-2'-ethenyl;

the intersystem crossing enhancing substituent is independently selected from the group consisting of C$_6$H$_4$X, C$_6$H$_3$X$_2$, C$_6$H$_2$X$_3$, C$_6$HX$_4$, and C$_6$X$_5$ where X is independently F, Cl, Br or I; and the TPA chromophore is independently selected from the group consisting of the following structures TPA A through TPA H:

TPA A

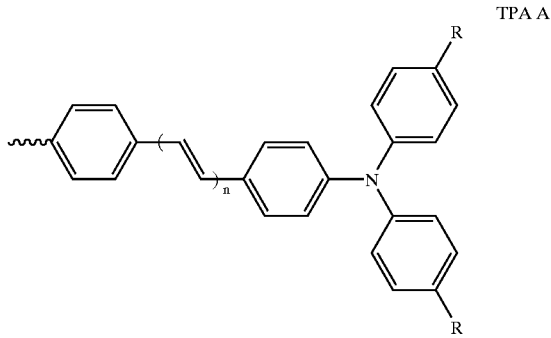

wherein in TPA A,
R is independently selected from the group consisting of H, alkyl, alkyloxy, and —(OCH$_2$CH$_2$)$_m$OG,
G is H or alkyl, and
m and n independently=1 to 5;

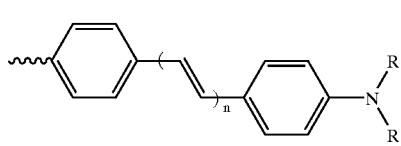

TPA B wherein in TPA B,
R is alkyl, and
n=1 to 5;

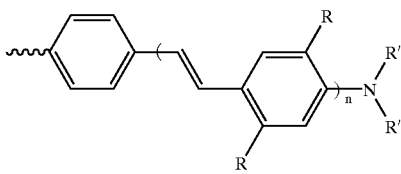

TPA C wherein in TPA C,
R is independently selected from the group consisting of H, CN, alkyl, and alkyloxy,
R' is independently selected from the group consisting of alkyl, alkyloxyphenyl, phenyl, and phenyl-$(OCH_2CH_2)_m$ OG,
G is H or alkyl, and
m and n independently=1 to 3;

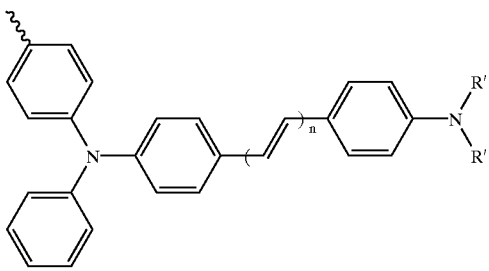

TPA D wherein in TPA D,
R' is independently selected from the group consisting of alkyl, alkyloxyphenyl, and phenyl-$(OCH_2CH_2)_m$OG,
G is H or alkyl, and
m and n independently=1 to 5;

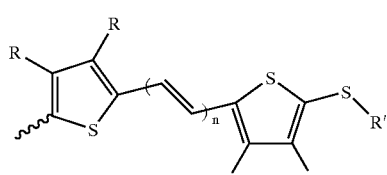

TPA E wherein in TPA E,
R is independently selected from the group consisting of H, alkyl, and —$(OCH_2CH_2)_m$OG,
R' is alkyl,
G is H or alkyl, and
m and n independently=1 to 5;

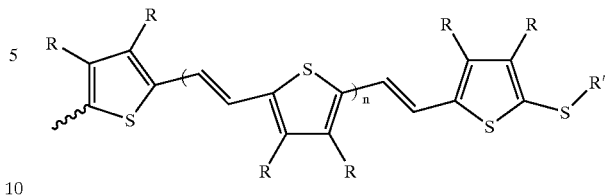

TPA F wherein in TPA F,
R is independently selected from the group consisting of H, alkyl, and —$(OCH_2CH_2)_m$OG,
R' is alkyl,
G is H or alkyl, and
m and n independently=1 to 3;

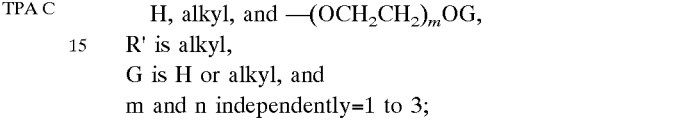

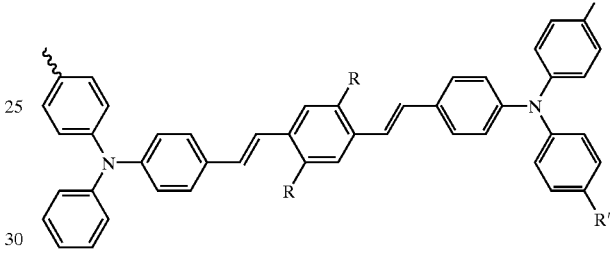

TPA G wherein in TPA G,
R is independently selected from the group consisting of H, CN, alkyl, alkyloxy, and —$(OCH_2CH_2)_m$OG,
R' is independently selected from the group consisting of H, alkyl, alkyloxy, and —$(OCH_2CH_2)_m$OG;
G is H or alkyl, and
m=1 to 6; and

TPA H

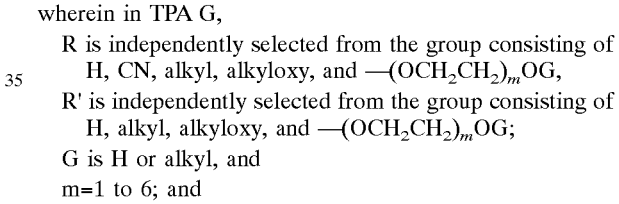

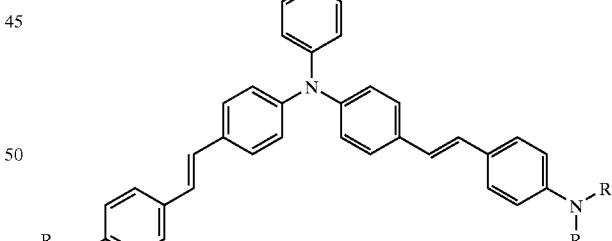

wherein in TPA H,
R is independently selected from the group consisting of alkyl, phenyl, alkyloxyphenyl, and phenyl[-$(OCH_2CH_2)_m$OG]$_x$,
G is H or alkyl,
m=1 to 4, and
x=1 to 4;
wherein in TPA A through H, alkyl is $C_1$ to $C_{20}$ and the selected TPA is attached to the porphyrin at the point indicated by the wiggle line.

7. The method according to claim 6, wherein the increased multi-photon absorption cross-section of the porphyrin-containing photosensitizer is at least about 50 GM units at about its maximum wavelength for two-photon absorption.

8. The method according to claim 6, wherein the increased multi-photon absorption cross-section of the porphyrin-containing photosensitizer is at least about 70 GM units at about its maximum wavelength for two-photon absorption.

9. The method according to claim 6, wherein the porphyrin core of the porphyrin-containing photosensitizer is selected from the group consisting of porphyrin, chlorin, bacteriochlorin, and isobacteriochlorin.

10. The method according to claim 6, wherein the porphyrin-containing photosensitizer absorbs two photons of radiation in the range of about 700 nm to about 1300 nm.

11. The method according to claim 10, wherein the absorbed radiation is in a range of about 700 nm to about 1100 nm.

12. An improved method of conducting photodynamic therapy comprising administering a therapeutically effective amount of a photoactive compound to a subject and exposing an area to be treated within the subject to radiation with a wavelength ranging from between about 700 nm to about 1300, wherein the improvement comprises administering a therapeutically effective amount of a photoactive compound of the following porphyrin structure:

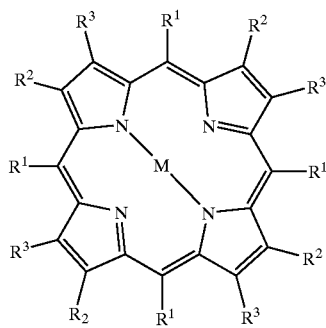

or any pharmaceutically acceptable salt thereof,
wherein
$R^1$ is independently -TPA, -L-TPA, —H, —Ar, —$(CH_2)_n$ $CH_3$, —CH═$CH_2$, —$(CH_2O)_n$-G, -t-Butyl, or —C(O) OG;

$R^2$ is independently -TPA, -L-TPA, —H, —Ar, —$(CH_2)_n$ $GH_3$, —CH═$CH_2$, —$(CH_2O)_n$-G, -t-Butyl, or —C(O) OG;

$R^3$ is independently -TPA, -L-TPA, —H, —Ar, —$(CH_2)_n$ $CH_3$, —CH═$CH_2$, —$(CH_2O)_n$-G, -t-Butyl, or —C(O) OG;

or independently $R^2$ and $R^3$ are linked by —$C_4H_4$— to form a six-membered ring;

M is either two hydrogen atoms or a metal ion;

n is independently an integer ranging from 1 to 20;

G is independently —H, or a $C_1$ to $C_{20}$ alkyl;

TPA is independently selected from the group consisting of the following structures TPA A through TPA H:

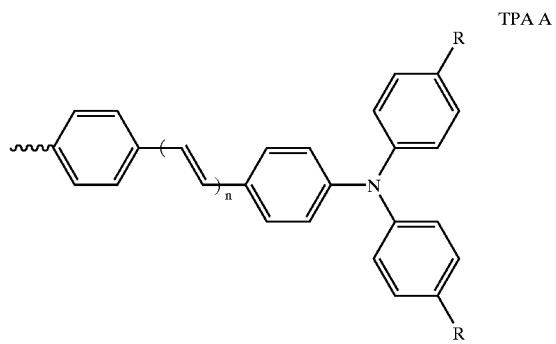

wherein in TPA A,
R is independently selected from the group consisting of H, alkyl, alkyloxy, and —$OCH_2CH_2)_m OG$,
G is H or alkyl, and
m and n independently=1 to 5;

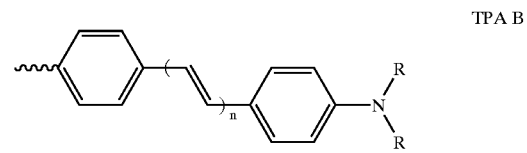

wherein in TPA B,
R is alkyl, and
n=1 to 5;

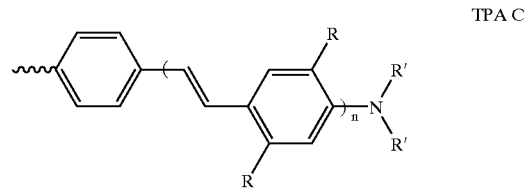

wherein in TPA C,
R is independently selected from the group consisting of H, CN, alkyl, and alkyloxy,
R' is independently selected from the group consisting of alkyl, alkyloxyphenyl, phenyl, and phenyl-$(OCH_2CH_2)_m OG$,
G is H or alkyl, and
m and n independently=1 to 3;

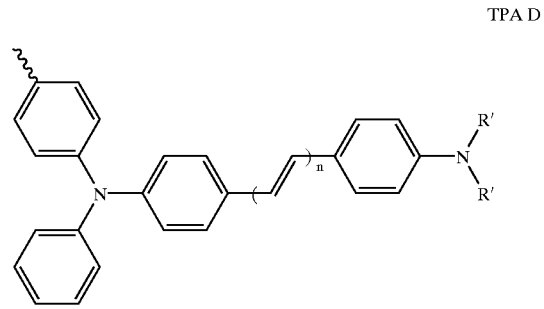

wherein in TPA D,
R' is independently selected from the group consisting of alkyl, alkyloxyphenyl, and phenyl-$(OCH_2CH_2)_m OG$, G is H or alkyl, and
m and n independently=1 to 5;

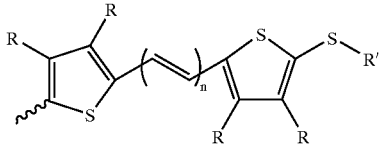
TPA E wherein in TPA E,
R is independently selected from the group consisting of H, alkyl, and —(OCH$_2$CH$_2$)$_m$OG,
R' is alkyl,
G is H or alkyl, and
m and n independently=1 to 5;

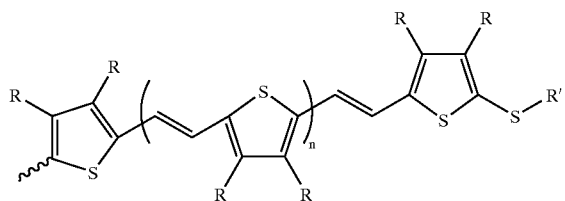
TAP F wherein in TPA F,
R is independently selected from the group consisting of H, alkyl, and —(OCH$_2$CH$_2$)$_m$OG,
R' is alkyl,
G is H or alkyl, and
m and n independently=1 to 3;

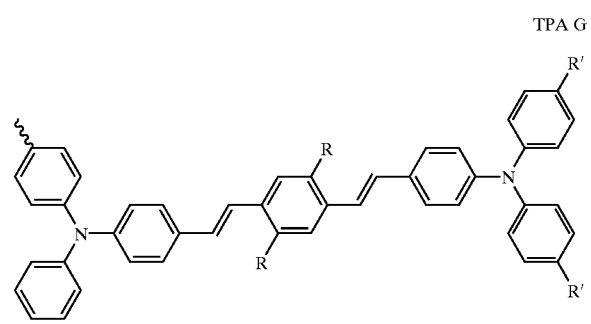
TPA G wherein in TPA G,
R is independently selected from the group consisting of H, CN, alkyl, alkyloxy, and —(OCH$_2$CH$_2$)$_m$OG,
R' is independently selected from the group consisting of H, alkyl, alkyloxy, and —(OCH$_2$CH$_2$)$_m$OG, G is H or alkyl, and
m=1 to 6; and

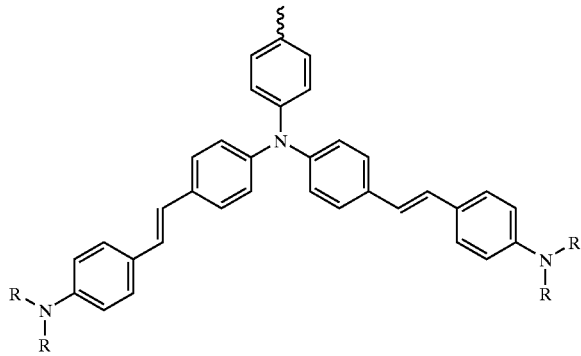
TPA H wherein in TPA H,
R is independently selected from the group consisting of alkyl, phenyl, alkyloxyphenyl, and phenyl-[(OCH$_2$CH$_2$)$_m$OG]$_x$,
G is H or alkyl,
m=1 to 4, and
x=1 to 4;
wherein in TPA A through H, alkyl is C$_1$ to C$_{20}$ and the selected TPA is attached to the porphyrin structure at the point indicated by the wiggle line;
Ar is independently C$_6$H$_4$X, C$_6$H$_3$X$_2$, C$_6$H$_2$X$_3$, C$_6$HX$_4$, or C$_6$X$_5$, wherein X is independently F, Cl, Br, or I; and
L is a linking moiety between the porphyrin structure and the TPA and is independently selected from the group consisting of ethenyl, ethynyl, —(CH$_2$)$_n$— where n is equal to 1 to 20, ortho-phenyl, meta-phenyl, para-phenyl, —C(=O)—O—, and 4-phenyl-2'-ethynyl;
wherein at least one of R$^1$, R$^2$ or R$^3$ is a -TPA or -L-TPA moiety, and at least one of R$^1$, R$^2$ or R$^3$ is not H or a -TPA or -L-TPA moiety.

13. The method according to claim 12, wherein the compound is 5-[4'''-(diphenylamino)-4''-stilbenyl]-15-[2',6'-dichlorophenyl]-21H, 23H-porphyrin.

14. The method according to claim 12, wherein M is a metal atom.

15. The method according to claim 12, wherein M is two hydrogen atoms.

16. The method according to claim 12, wherein a therapeutically effective amount ranges from about 0.1 mg to about 10 mg per kg of body weight.

* * * * *

UNITED STATES PATENT AND TRADEMARK OFFICE
CERTIFICATE OF CORRECTION

| | | |
|---|---|---|
| PATENT NO. | : 6,953,570 B2 | Page 1 of 1 |
| APPLICATION NO. | : 10/225303 | |
| DATED | : October 11, 2005 | |
| INVENTOR(S) | : Nickel et al. | |

It is certified that error appears in the above-identified patent and that said Letters Patent is hereby corrected as shown below:

At Column 25, line 31: should read --form a six-member<u>ed</u> ring--,
At Column 26, line 45: should read --alkyl, alkyloxyphenyl, and phenyl-<u>(OCH$_2$CH$_2$)$_m$OG</u>(~~OCH$_2$CH$_2$)$_m$OG~~--,
At Column 26, line 63: should read --H, alkyl, and —(OCH$_2$CH$_2$)$_m$OG--,
At Column 31, line 54: should read --~~CH$_3$~~<u>CH$_3$</u>, —CH=CH$_2$, —(CH$_2$O)$_n$-G, -t-Butyl, or —C(O)--,
At Column 32, line 18: should read --H, alkyl, alkyloxy, and —(OCH$_2$CH$_2$)$_m$OG--, Signed and Sealed this Fourth Day of November, 2008

JON W. DUDAS
*Director of the United States Patent and Trademark Office*